United States Patent
Humphries et al.

(10) Patent No.: US 12,054,719 B2
(45) Date of Patent: Aug. 6, 2024

(54) RNAi THERAPY FOR TREATMENT AND/OR PREVENTION OF GLAUCOMA

(71) Applicants: THE PROVOST, FELLOWS, FOUNDATION SCHOLARS, & THE OTHER MEMBERS OF BOARD, OF THE COLLEGE OF THE HOLY & UNDIV. TRINITY OF QUEEN ELIZABETH NEARD DUBLIN, Dublin (IE); IMPERIAL COLLEGE INNOVATIONS LIMITED, London (GB); DUKE UNIVERSITY, Durham, NC (US)

(72) Inventors: Peter Humphries, Dublin (IE); Marian Humphries, Dublin (IE); Matthew Campbell, Dublin (IE); Anna-Sophia Kiang, Bray (IE); Daniel Stamer, Durham, NC (US); Darryl Ray Overby, London (GB); Chi Shing Lawrence Tam, Dublin (IE)

(73) Assignees: PROV FELLOWS COLLEGE HOLY TRINITY QUEEN ELIZABETH, Dublin (IE); IMPERIAL COLLEGE INNOVATIONS LIMITED, London (GB); DUKE UNIVERSITY, Durham, NC (US)

( * ) Notice: Subject to any disclaimer, the term of this patent is extended or adjusted under 35 U.S.C. 154(b) by 604 days.

(21) Appl. No.: 16/099,153

(22) PCT Filed: Apr. 28, 2017

(86) PCT No.: PCT/EP2017/060301
§ 371 (c)(1),
(2) Date: Nov. 5, 2018

(87) PCT Pub. No.: WO2017/191077
PCT Pub. Date: Nov. 9, 2017

(65) Prior Publication Data
US 2019/0376065 A1   Dec. 12, 2019

(30) Foreign Application Priority Data

May 4, 2016 (GB) ...................... 1607797

(51) Int. Cl.
*C07H 21/02* (2006.01)
*A61P 27/06* (2006.01)
*C07H 21/04* (2006.01)
*C12N 15/113* (2010.01)

(52) U.S. Cl.
CPC .......... *C12N 15/1138* (2013.01); *A61P 27/06* (2018.01); *C12N 15/113* (2013.01); *C12N 2310/122* (2013.01); *C12N 2310/14* (2013.01); *C12N 2310/531* (2013.01); *C12N 2320/30* (2013.01); *C12N 2320/32* (2013.01)

(58) Field of Classification Search
CPC ............ C12N 2320/30; C12N 2310/14; C12N 15/113
See application file for complete search history.

(56) References Cited

U.S. PATENT DOCUMENTS

2009/0192105 A1* 7/2009 McSwiggen ........... C07H 21/04
                                                                        514/44 R

FOREIGN PATENT DOCUMENTS

WO   WO2009/047362   4/2009

OTHER PUBLICATIONS

Thakur et al. (Journal of Biological Engineering, 2012, 6:7, pp. 1-16).*
Gonzalez-Mariscal et al. (J. Membrane Biol., 207, 55-68, 2005).*
Gorbatyuk et al. (Vision Research, 2007, 47, 9, 1202-1208).*
Yang et al. (J. Glaucoma, 2015, 24(4), 291-296).*

* cited by examiner

*Primary Examiner* — Amy Rose Hudson
(74) *Attorney, Agent, or Firm* — Hovey Williams LLP; Crissa A. Cook

(57) ABSTRACT

The present invention is directed to an RNAi-inducing agent capable of reducing and/or inhibiting the expression of proteins associated with the tight junction complex joining Schlemm's canal endothelial cells (SCEC) in the eye of a subject for use in the prevention and/or treatment of glaucoma. Specifically, the RNAi-inducing agent is capable of reducing and/or inhibiting the expression of proteins expressed in the tight junction complex or supporting the tight junction complex joining Schlemm's canal endothelial cells (SCEC) in the eye of a subject for use in the prevention and/or treatment of glaucoma. Methods using this RNAi-inducing agent are also contemplated.

12 Claims, 13 Drawing Sheets
Specification includes a Sequence Listing.

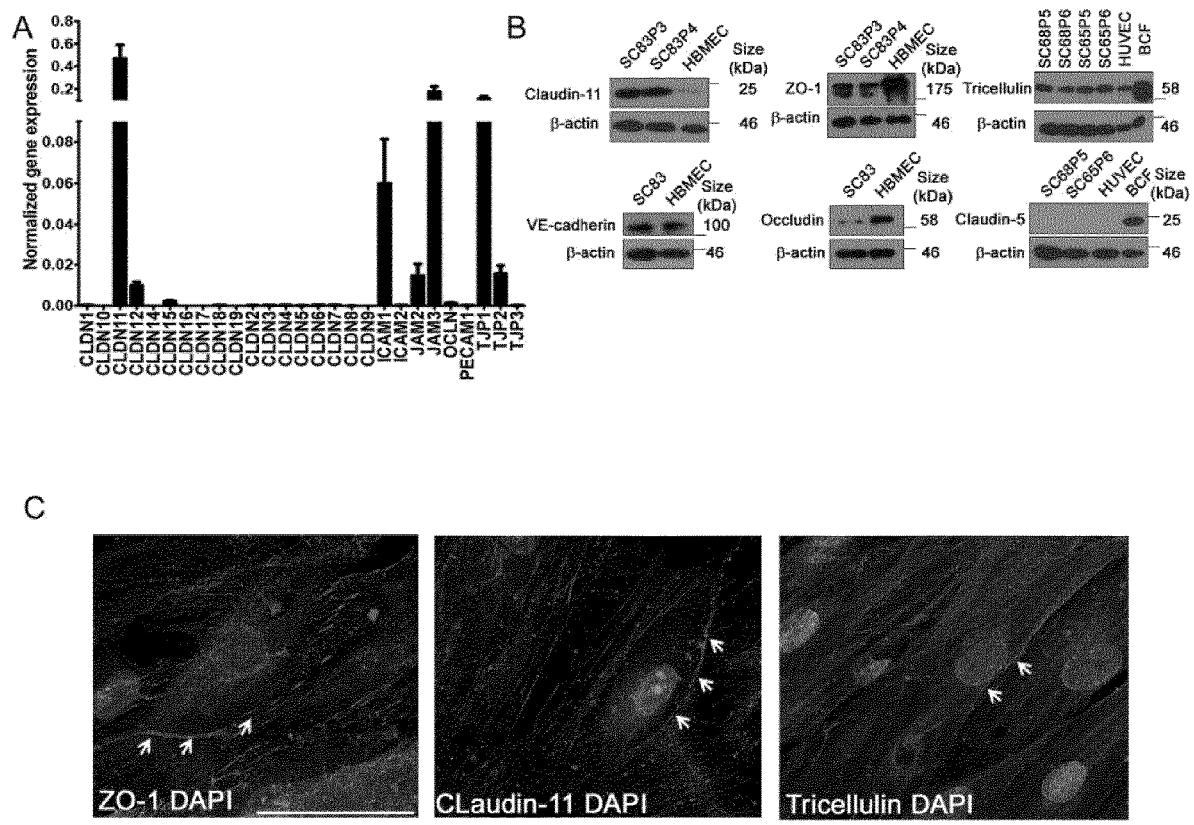
Figure 2a-c

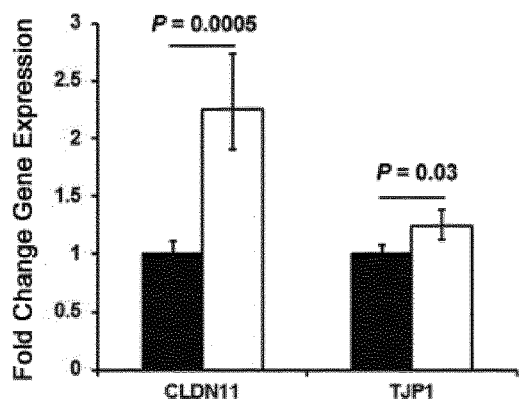
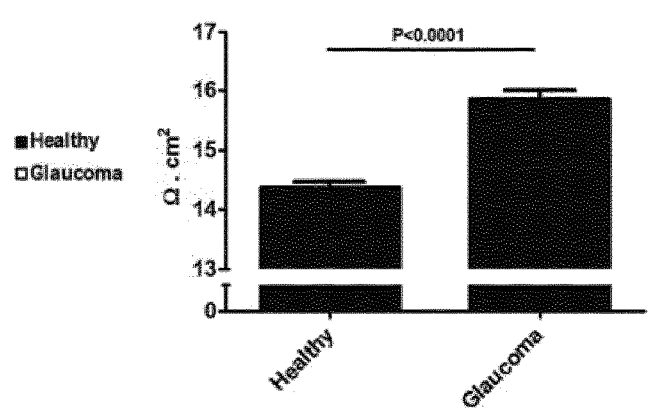
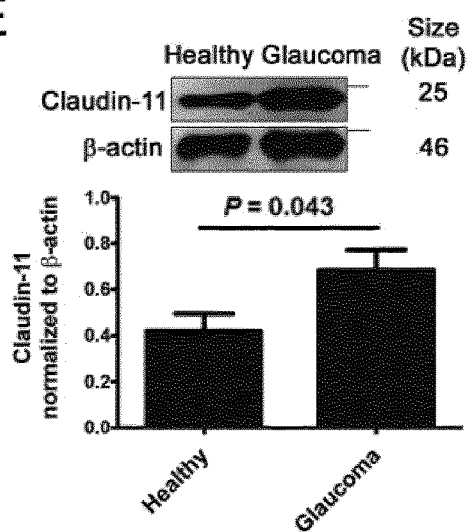
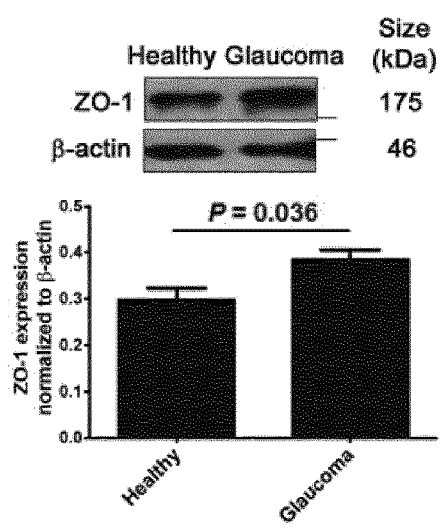
Figure 2d-f

RNAi THERAPY FOR TREATMENT AND/OR PREVENTION OF GLAUCOMA

CROSS-REFERENCE TO RELATED APPLICATIONS

This application claims the benefit and priority of GB Patent Application No. 1607797.6., filed May 4, 2016, and of International Application No. PCT/EP2017/060301. The contents of both applications are hereby incorporated by reference in their entirety.

STATEMENT OF FEDERAL FUNDING

Not applicable.

PARTIES TO JOINT RESEARCH AGREEMENT

Not applicable.

REFERENCE TO SEQUENCE LISTING OR TABLE SUBMITTED ON COMPACT DISC AND INCORPORATION-BY-REFERENCE OF THE MATERIAL

The instant application contains a Sequence Listing which has been submitted electronically in ASCII format and is hereby incorporated by reference in its entirety. Said ASCII copy, created on Aug. 30, 2019, is named FR3_8_30_SeqListing_ST25 and is 4 kilobytes in size.

This invention relates to an RNAi-inducing agent capable of reducing and/or inhibiting the expression of one or more tight junction proteins expressed in or associated with the tight junction complex joining Schlemm's canal endothelial cells (SCEC) in the eye for use in the prevention and/or treatment of glaucoma, particularly by reduction of intra-ocular pressure, and a method of treatment thereof.

BACKGROUND TO THE INVENTION

Glaucoma is a chronic neurodegenerative pathology characterized by progressive loss of retinal ganglion cells and structural changes of the optic nerve head. It represents the second leading cause of visual handicap worldwide where it is estimated that 65 million people currently have glaucoma and is the most common form of incurable blindness. The most common form, primary open-angle glaucoma, has as main risk factor the increase of intraocular pressure (IOP).

Maintenance of intraocular pressure (IOP) at physiological levels is essential for the general health of the human eye. Correct intraocular pressure (IOP) at 12-15 mm Hg is maintained by a balance of fluid production (aqueous humor) and its removal through the drainage channels at the front of the eye. IOP is governed by the rate of aqueous humour production by the ciliary process and drainage from the anterior segment via the two main outflow pathways: conventional and unconventional.

Under physiological conditions, the majority of aqueous humour exits the anterior chamber through the conventional outflow pathway in humans. In this pathway, aqueous humour filters sequentially through the trabecular meshwork (TM), including the juxtacanalicular tissue (JCT), and the endothelial lining of Schlemm's canal (SC) before entering the SC lumen that drains to the episcleral veins. Electron microscopic evidence has indicated that aqueous humour drainage across SC endothelium occurs through micron-sized pores that pass either through (transcellular) or between (paracellular) individual SC cells. In particular, a significant fraction of aqueous humor crosses the inner wall of SC via paracellular pores. Moreover, the presence of tight-, adherens- and gap-junctions in SC endothelial cells provides a mechanism by which the conventional outflow pathway is dynamically responsive to constantly changing physiological conditions while still preserving the blood-aqueous barrier. However, the removal of aqueous humor through the drainage channels at the front of the eye does not always function optimally and results in elevated ocular pressure which damages the optic nerve and if untreated leads to blindness. It has long been recognised that elevated IOP associated with primary open-angle glaucoma (POAG) is due to elevated resistance to aqueous humour outflow through the conventional outflow pathway, although the cause of outflow elevated resistance in glaucoma remains to be fully elucidated. Previous studies support the concept that outflow resistance is modulated through a synergistic hydro-dynamic interaction between JCT and SC endothelium such that inner wall pore density may influence outflow resistance generation by defining the regions of filtration through the JCT. As glaucomatous eyes have reduced SC inner pore density, decreased porosity of the inner wall appears to contribute to elevated outflow resistance and increased IOP. Prolonged elevation of IOP results in progressive degeneration of retinal ganglion cell axons, and subsequently leads to vision loss.

Treatment of POAG by lowering IOP remains the major approach to limiting disease progression. Topically-applied medications that either reduce aqueous humor production or increase drainage through the unconventional outflow pathway, including carbonic anhydrase inhibitors, adrenergic mimetics and prostaglandin analogues, are widely and successfully used in management of IOP in patients with POAG. However, a proportion of POAG patients fail to reach target IOP lowering using current medications, and invasive surgical interventions such as trabeculectomy, argon laser trabeculoplasty or canaloplasty are required to lower IOP. The overall annual cost of clinical management in US has been recently estimated at approx. $1.9 billion, with up to 50% of such costs related to topical pressure reducing medications. Furthermore, it is estimated that up to approximately 10% of cases of open-angle glaucoma patients do not respond adequately to available intraocular pressure (IOP)-reducing topical medications or become resistant to such conventional treatments.

Thus, there is a need for the development of alternative means of controlling glaucoma and associated IOP/ocular hypertension.

STATEMENTS OF THE INVENTION

In general, the present invention is directed to a method and use of RNA interference (RNAi), using RNAi inducing agents, whose presence within a cell results in production of an siRNA or shRNA, targeting tight junction proteins expressed in the tight junction complex joining Schlemm's canal endothelial cells (SCEC) in the eye, for the transient, reversible and controlled opening of these tight junctions. Advantageously, this method and use can be used for the prevention and/or treatment of glaucoma, particularly by reducing elevated IOP (ocular hypertension) within the eye. Alternatively, this method can be used for the reduction of intra-ocular pressure and/or for treating ocular hypertension not associated with glaucoma.

In a general context, the present invention is directed to an RNAi-inducing agent capable of reducing and/or inhibiting the expression of proteins associated with the tight junction complex joining Schlemm's canal endothelial cells (SCEC) in the eye of a subject for use in the prevention and/or treatment of glaucoma. Specifically, the RNAi-inducing agent is capable of reducing and/or inhibiting the expression of proteins expressed in the tight junction complex or supporting the tight junction complex joining Schlemm's canal endothelial cells (SCEC) in the eye of a subject for use in the prevention and/or treatment of glaucoma.

According to a first aspect of the invention, there is provided an RNAi-inducing agent capable of reducing and/or inhibiting the expression of one or more tight junction proteins expressed in the tight junction complex joining Schlemm's canal endothelial cells (SCEC) in the eye for use in the prevention and/or treatment of glaucoma, reduction of intra-ocular pressure and/or for treating ocular hypertension in a subject in need thereof.

Additionally or alternatively, there is provided an RNAi-inducing agent capable of reducing and/or inhibiting the expression of adherens junction proteins, such as VE-cadherin and platelet endothelial cell adhesion molecule (PECAM-1), which are coupled to and/or provide support to the tight junction complex joining Schlemm's canal endothelial cells (SCEC) in the eye for use in the prevention and/or treatment of glaucoma, reduction of intra-ocular pressure and/or for treating ocular hypertension in a subject in need thereof. This aspect of the invention is based on the observation that both VE-cadherin and platelet endothelial cell adhesion molecule (PECAM-1) are expressed in SC cells (Heimark R L, Kaochar S, Stamer W D (2002) Human Schlemm's canal cells express the endothelial aderens proteins, VE-cadherin and PECAM-1. Curr. Eye. Res. 25(5). 299-308).

It is thought that the assembly of adherens junctions is required for the correct organisation of tight junctions (Bazzoni G and Dejana E (2004) Endothelial cell-to-cell junctions: molecular organisation and role in vascular homeostasis. Physiol Rev. 84. 869-901). Accordingly, this method provides an alternative means to achieve a similar reduction or disassembly of the tight junction complex joining Schlemm's canal endothelial cells (SCEC) in the eye by silencing proteins present in a separate cellular structure known as the adherens junction that are coupled to and provide mechanical support to the tight junction complex joining Schlemm's canal endothelial cells (SCEC). On this basis, an RNAi-inducing agent/siRNA may be designed that targets VE-cadherin, which is an adherens junction protein that is highly expressed by SCECs or an RNAi-inducing agent/siRNA may be designed that targets platelet endothelial cell adhesion molecule (PECAM-1). In essence, this is an indirect route to achieving similar effect on tight junction permeability without directly targeting the tight junction complex joining Schlemm's canal endothelial cells (SCEC).

According to a second aspect of the invention, there is provided a method for the prevention and/or treatment of glaucoma in a subject comprising the step of administering an effective amount of an RNAi inducing agent capable of reducing and/or inhibiting the expression of one or more tight junction proteins expressed in the tight junction complex joining Schlemm's canal endothelial cells (SCEC) in the eye of the subject.

According to a third aspect of the invention, there is provided a method for reducing intra-ocular pressure in a subject in need thereof comprising administering an effective amount of an RNAi inducing agent capable of reducing and/or inhibiting the expression of one or more tight junction proteins expressed in the tight junction complex joining Schlemm's canal endothelial cells (SCEC) in the eye of the subject.

According to a fourth aspect of the invention, there is provided a method for treating ocular hypertension in a subject in need thereof comprising administering an effective amount of an RNAi inducing agent capable of reducing and/or inhibiting the expression of one or more tight junction proteins expressed in the tight junction complex joining Schlemm's canal endothelial cells (SCEC) in the eye of the subject.

DETAILED DESCRIPTION OF THE INVENTION

It will be understood that the present invention is directed to a method for the treatment of glaucoma, particularly glaucoma associated elevated intra-ocular pressure or ocular hypertension. Where a subject has an increased IOP but does not show the other signs of glaucoma, this is commonly referred to as ocular hypertension. Preferably, the present invention is directed to a method which targets symptoms associated with glaucoma such as increased intra-ocular pressure/ocular hypertension. However, the invention is also applicable to the reduction of intra-ocular pressure and/or for treating ocular hypertension not associated with glaucoma.

It will be understood that tight junction proteins expressed in the tight junction complex joining Schlemm's canal endothelial cells (SCEC) in the eye include claudins, occludin, Zonula Occludens-1 Protein (TJP1), Zonula Occludens-2 Protein. Preferred tight junction proteins include claudin proteins, such as claudin-11, Tricellulin and ZO-1.

Adherens junctions are protein complexes that occur at cell-cell junctions in epithelial and endothelial tissues. In this specification, it will be understood that adherens junction proteins include proteins such as cadherins such as VE-cadherin and platelet endothelial cell adhesion molecule (PECAM-1). Other adherens junction proteins include p120, γ-catenin and α-catenin.

RNA Interference

The art of silencing or "knocking down" gene expression, by degradation of mRNA or other effects, is well known. Examples of technologies developed for this purpose include siRNA, miRNA, shRNA, shmiRNA, and dsRNA. A comprehensive overview of this field can be found in Singh M S and Peer D. RNA Nanomedicines: the next generation of drugs. Curr. Opin. Biotech. 2016 Jan. 8; 39: 28-34 and Bobbin M L and Rossi J J (2016) 'RNA Interference (RNAi)-Based Therapeutics: Delivering on the Promise?' Annu Rev Pharmacol Toxicol. 6. 103-122.

In this specification, it will be understood that the terms siRNA and RNAi are interchangeable. An "RNAi-inducing agent" or "RNAi molecule" is used in the invention and includes for example, siRNA, miRNA or shRNA targeted to a target transcript or an RNAi-inducing vector (e.g. AAV/lentivirus vector expressing shRNA) whose presence within a cell results in production of an siRNA or shRNA targeted to a target transcript. Such siRNA or shRNA comprises a portion of RNA that is complementary to a region of the target transcript. An important feature of RNAi affected by siRNA is the double stranded nature of the RNA and the absence of large overhanging pieces of single stranded RNA, although dsRNA with small overhangs and with intervening loops of RNA has been shown to effect suppression of a target gene. In this specification, it will be understood that in this specification the terms siRNA and RNAi are interchangeable. Such siRNA or shRNA comprises a portion of RNA that is complementary to a region of the target transcript. Essentially, the "RNAi-inducing agent" or "RNAi molecule" downregulates expression of the targeted tight junction proteins via RNA interference.

Essentially, the "RNAi-inducing agent" or "RNAi molecule" downregulates expression of the targeted tight junction proteins via RNA interference. In this manner, small RNA molecules, such as small interfering RNAs (siRNA), interact sequence-specifically with complementary mRNAs of targeted genes, leading to the degradation of this mRNA and thereby preventing the production of the corresponding protein. Such RNAi inducing agents can be single or double stranded. Preferably, one strand of a double-stranded RNAi-inducing agent comprises at least a partial sequence complementary to a target mRNA. The nucleotides of the inhibitory nucleic acid can be chemically modified, natural or artificial. The sequence homology between the RNAi inducing agent and the targeted tight junction mRNA may be 100% or less, but is ideally greater than about 50% and typically 90% or greater and even more preferably at least 98% and 99%. It will be understood that the percentage of sequence homology between RNAi inducing agent and the target mRNA should be sufficient to result in sequence specific association between the RNAi inducing agent, e.g. siRNA, and the target mRNA, preferably under cytoplasmic conditions.

Such siRNAs comprise two RNA strands having a region of complementarity of approximately 20 or so nucleotides in length and optionally further comprises one or two single-stranded overhangs or loops. In mammalian cells, dsRNA longer than 30 base pairs can cause non-specific gene suppression by an interferon a response. However, cells transfected with 21 nucleotide synthetic double-stranded siRNA bearing two nucleotides protruding at both 3'-ends have been found to escape an interferon response and effectively exert sequence-specific gene silencing function. The silencing effect of the synthetic siRNA, however, is transient. The double stranded siRNA molecule down regulates expression of the tight junctions of the blood brain barrier and/or the blood retinal barrier via RNAi, wherein each strand of said siRNA molecule is independently about 18 to about 28 nucleotides in length and one strand of the siRNA molecule comprises a nucleotide sequence having sufficient complementarity to the RNA of the target tight junction protein or proteins for the siRNA molecule to direct cleavage of the target RNA via RNA interference.

In shRNA, the single RNA strand may form a hairpin structure with a stem and loop and, optionally, one or more unpaired portions at the 5' and/or 3' portion of the RNA.

RNA interference (RNAi) agents, particularly siRNAs, can be delivered to the target cell exogenously or expressed endogenously in the form of short hairpin RNAs (shRNAs).

Specifically, the method involves the delivery of an effective amount of siRNA or shRNA targeting tight junction proteins in the subject. It will be understood that an effective amount of the RNAi-inducing agent, such as siRNA, is used to target and down-regulate the tight junction proteins expressed in the tight junction complex joining Schlemm's canal endothelial cells (SCEC) in the eye.

The present invention provides means and methods for the prevention or treatment of glaucoma by using an RNA interference (RNAi) agent directed against mRNA transcripts encoding one or more tight junction proteins expressed in the tight junction complex joining Schlemm's canal endothelial cells (SCEC) in the eye. In this manner the RNAi-inducing agent is capable of inhibiting the expression of one or more tight junction proteins expressed in the tight junction complex joining Schlemm's canal endothelial cells (SCEC) in the eye at the mRNA level. According to a general aspect of the invention, there is provided an RNAi-inducing agent capable of reducing and/or inhibiting (i.e. targeting) the expression of one or more tight junction proteins expressed in the tight junction complex joining Schlemm's canal endothelial cells (SCEC) in the eye for use in the prevention and/or treatment of glaucoma. Advantageously, this treatment directly targets the diseased tissue responsible for IOP elevation, reduces the intra-ocular pressure in the subject and/or treats ocular hypertension.

As disclosed in PCT/EP2008/063734, the contents of which are incorporated by reference, it is possible to increase the permeability of endothelial cells lining the cerebral and inner retinal vasculatures by using a technique involving RNAi-mediated down-regulation of transcripts encoding claudin-5, a major component of the tight junctions (TJ) of such endothelial cells. Using this technique, the blood-brain and inner blood-retina barriers are rendered reversibly permeable to systemically-administered compounds of up to approximately 1 kDa in molecular weight, thereby facilitating systemic drug access and enabling reduction of pathological cerebral edema. Moreover, simultaneous suppression of claudin-5 and occludin within the inner retinal vascular endothelia permits soluble amyloid 11-40 (molecular weight 4.33 kDa) to be removed from retinal tissues into the peripheral circulation (Keaney J. et al. Autoregulated paracellular clearance of amyloid-β across the blood-brain barrier. SciAdv. 1, e1500472 (2015). We have now surprisingly shown that down-regulation of selected TJ components of endothelial cells lining the inner wall of SC increases the paracellular spaces between these cells, facilitating flow of aqueous humor across the inner wall into the SC (FIG. 1). Based on our results, we postulate that owing to the fact that a major fraction of aqueous humour filtration at the level of SC appears to largely pass through paracellular routes, strategies targeting cell-cell junctions between endothelial cells of the inner wall of SC may be most effective at decreasing outflow resistance, reducing intra-ocular pressure and/or treating ocular hypertension in a subject.

We have also identified TJ components in human primary cultures of SC endothelial cells (SCEC), and also in mouse and non-human primate outflow tissues that act as preferential targets for the invention. A previous study has demonstrated ZO-1 expression in human SCEC (Alvarado et al., 2004. Endothelia of Schlemm's canal and trabecular meshwork: distinct molecular, functional, and anatomic features. Am J Physiol Cell Physiol. JAM-3 and ICAM-1 have also been found to be expressed in SCEC. Our studies show for the first time that claudin-11 and tricellulin tight junction proteins are expressed in cultured human SCEC, and also in non-human primate outflow tissues. For these reasons, we propose that claudin-11 mRNA (NM_005602), Tricellulin mRNA (NM_001038603), junctional adhesion molecule-3 (JAM-3), intercellular adhesion molecule-1 and/or ZO-1 mRNA (NM_003257) are targets for down-regulation.

Advantageously, we have now shown that siRNA-mediated down-regulation of the TJ components of the SCEC increases the paracellular permeability of human primary SCEC to less than 200 kDa, preferably less than 150 kDa, more preferably less than 100 KDa, ideally less than approximately 70 kDa. In addition to the advantages in decreasing outflow resistance, reducing intra-ocular pressure and/or treating ocular hypertension in a subject, it will be understood that this method may also provide a means to deliver a therapy (such as a drug or other ocular treatment composition) to the eye, in particular to the Schlemm's canal endothelial cells (SCEC) in the eye of the subject.

We have also shown that siRNA-mediated down-regulation of the TJ components of the SCEC decreases transendothelial electrical resistance. Furthermore, we show that intracameral delivery of siRNAs targeting selected TJ components reduces IOP and elevates outflow facility (the mathematical inverse of outflow resistance), with a concomitant increase in intercellular spaces between SC inner wall endothelial cells. Our findings indicate that manipulation of TJs within the conventional outflow pathway provides a new means of promoting aqueous humour outflow. This is particularly important in cases of POAG that are resistant or non-responsive to conventional pressure lowering medications.

The juxtacanalicular connective tissue of the trabecular meshwork together with the inner wall endothelium of Schlemm's canal (SC) provide the majority of resistance to outflow of aqueous humour from the anterior chamber of the eye, and therefore regulate IOP. We addressed the hypothesis that down-regulation of transcripts encoding selected components of the tight junction (TJ) complex joining SC endothelial cells (SCEC) would increase their permeability, facilitating aqueous outflow and providing a novel avenue for reducing intraocular pressure. We showed that siRNA-mediated suppression of transcripts encoding tight junction components claudin-11, zonula-occludens-1 (ZO-1) and tricellulin in human SCEC monolayers in vitro resulted in increased paracellular permeability. Intracameral injection in mice of siRNAs validated against ZO-1 and tricellulin increased outflow facility, and reduced IOP. Ultrastructural analysis of the inner wall of Schlemm's canal by transmission electron microscopy revealed disconnections of parts of the inner wall with enlarged intercellular gaps between SCEC, suggestive of a widening of paracellular routes following knockdown of TJs. These data suggest that the continuity of SC endothelium is a principle determinant of outflow resistance and that direct manipulation of SC endothelial TJs provides a novel means of controlling aqueous outflow in cases of open-angle glaucoma that will be additive to currently prescribed medications The present inventors have found that the proteins Claudin-11, Tricellulin and ZO-1 are prominant tight junction proteins expressed in the tight junction complex joining Schlemm's canal endothelial cells in the eye. Our study shows for the first time that claudin-11 and tricellulin are expressed in SCEC, whereas ZO-1 has previously been shown to be expressed in SCEC. We postulate that junctional adhesion molecule-3 (JAM-3) and intercellular adhesion molecule-1 (ICAM-1) will act in a similar manner and are also potential targets for RNA interference. Claudin-11, tricellulin and ZO-1 were selected based on their expression levels in SCEC, as well as their roles in regulating cellular permeability in other cell systems.

Thus, according to one embodiment of the invention, the RNAi inducing agent is capable of reducing and/or inhibiting the expression of one or more of tight junction proteins claudin-11, Tricellulin, ZO-1, junctional adhesion molecule-3 (JAM-3) or intercellular adhesion molecule-1 (ICAM-1).

For example, the RNAi inducing agent is capable of reducing and/or inhibiting the expression of each tight junction proteins claudin-11, Tricellulin, ZO-1 junctional adhesion molecule-3 (JAM-3) or intercellular adhesion molecule-1 (ICAM-1) separately, in pairs or all together.

Preferably, the RNAi inducing agent is capable of reducing and/or inhibiting the expression of at least one of tight junction proteins claudin-11, Tricellulin or ZO-1.

More preferably, the RNAi inducing agent is capable of reducing and/or inhibiting the expression of two or more of tight junction proteins claudin-11, Tricellulin or ZO-1.

Still more preferably, the RNAi inducing agent is capable of reducing and/or inhibiting the expression of tight junction proteins claudin-11, Tricellulin and ZO-1.

We have shown that a combination of claudin-11 and ZO-1 siRNAs is more effective than the use of claudin-11 or ZO-1 siRNA singly (FIG. 4d). Furthermore, a combination of ZO-1 and tricellulin is more effective than the use of single siRNAs (FIG. 4e).

The techniques of designing siRNA are well known to those skilled in the art and will not be expanded on in detail here. Ideally, the siRNA is selected from conserved regions of the respective genes.

Some non-limiting examples of target DNA sequences in the target genes used in the generation of the siRNA sequences are highlighted below (overhangs in lower case and underlined):

```
human claudin-11 siRNA (5'-gtcatttacttgtacgaga-3'
(SEQ ID NO: 1), ID number: s9925);

(SEQ ID NO: 2)
Sense (5' → 3') GTCATTTACTTGTACGAGAtt (SEQ ID NO: 3)
Antisense (5' → 3') TCTCGTACAAGTAAATGACct human ZO-1 siRNA (5'-cgatctcataaacttcgta-3'
(SEQ ID NO: 4), ID number: s14156);

(SEQ ID NO: 5)
Sense (5' → 3') CGATCTCATAAACTTCGTAtt (SEQ ID NO: 6)
Antisense (5' → 3') TACGAAGTTTATGAGATCGct human MARVELD2 siRNA (5'-ggattagcttggatcacca-3'
(SEQ ID NO: 7), ID number: s45794);

(SEQ ID NO: 8)
Sense (5' → 3') ACGAGAGAATTTCAAGAATtt (SEQ ID NO: 9)
Antisense (5'→ 3') ATTCTTGAAATTCTCTCGTtt mouse ZO-1 siRNA (5'-cattcgccttcatacaata-3'
(SEQ ID NO: 10), ID number: s75175;

(SEQ ID NO: 11)
Sense (5' → 3') CATTCGCCTTCATACAATAtt (SEQ ID NO: 12)
Antisense (5'→ 3') TATTGTATGAAGGCGAATGat mouse MARVELD2 siRNA (5'-acgagagaatttcaagaat-3'
(SEQ ID NO: 13), ID number:ADCSU2H).

(SEQ ID NO: 14)
Sense (5' → 3') GGATTAGCTTGGATCACCAtt (SEQ ID NO: 15)
Antisense (5' → 3') TGGTGATCCAAGCTAATCCag
``` shRNA may also be chosen to target these TJ proteins. shRNA targeting TJ proteins will ultimately have the same sense and anti-sense sequence as the siRNA. The only difference is that they contain short hairpins composed of the following nucleotides UAUCAAGAG which form a hairpin structure and allow for them to be cloned into delivery vectors.

It will be understood that typically the region of the siRNA sequence with sequence identity to the target mRNA, the tight junction protein transcripts, is from 14 to 30 nucleotides in length, for example from 16 to 24 nucleotides, more preferably from 18 to 22 nucleotides, most preferably from 19 to 21 nucleotides in length. The siRNA is sufficiently complementary to the target mRNA of the tight junction protein that the siRNA agent silences production of a protein encoded by the target mRNA.

The siRNA may be blunt ended or may have overhangs at its 3' or 5' termini, preferably at both of its termini. The overhangs are preferably short in length, for example less than 30 nucleotides, preferably less than 20 nucleotides more preferably less than 10 nucleotides, even more preferably less than 5 nucleotides, most preferably less than 3 nucleotides in length. Typically, the overhangs are two nucleotides in length.

Thus, the siRNAs of the invention are typically less than 30 nucleotides in length and can be single or double stranded. Longer siRNAs can comprise cleavage sites that can be enzymatically or chemically cleaved to produce siRNAs having lengths less than 30 nucleotides, typically 21 to 23 nucleotides as above. It will be understood that siRNAs share sequence homology with corresponding target mRNAs. The sequence homology can be 100% or less and should be sufficient to result is sequence specific association between the siRNA and the targeted mRNA. Exemplary siRNAs do not activate the interferon signal transduction pathway. The most preferred embodiment of the invention comprises a siRNA having 100% sequence identity with the target mRNA, the tight junction protein. However, other sequences with less than 100% homology (as described in relation to RNAi inducing agents in general) may be used wherein the siRNA is of sufficient homology to guide the RNA-induced silencing complex (RISC) to the target mRNA for degradation.

Limited mutations in siRNA relative to the target mRNA may also be contemplated. It will be understood that the siRNA of the present invention ideally has nucleotide overhangs. For example, the siRNA may have two nucleotide overhangs (e.g. UU), thus, the siRNA will comprise a 21 nucleotide sense strand and a 21 nucleotide antisense strand paired so as to have a 19 nucleotide duplex region. The number of nucleotides in the overhang can be in the range of about 1 to about 6 homologous nucleotide overhangs at each of the 5' and 3' ends, preferably, about 2 to 4, more preferably, about 3 homologous nucleotide overhangs at each of the 5' and 3' ends.

In addition, the siRNA may be chemically modified, for example, to be more stable upon administration and/or reduce immune response. Non-limiting examples include substitution at the 2'-OH ribose or alteration of the phosphodiester backbone. The nucleotides overhang can be modified, for example to increase nuclease resistance. For example, the 3' overhang can comprise 2' deoxynucleotides, e.g., TT, for improved nuclease resistance.

According to a preferred embodiment, the RNAi inducing agent is capable of reducing and/or inhibiting the expression of tight junction proteins claudin-11, Tricellulin and ZO-1. In this manner, the claudin-11, Tricellulin and ZO-1 may be administered simultaneously or sequentially. We have found that suppression of tight junction proteins claudin-11, Tricellulin and ZO-1 together provides better results, in terms of on loosening the junctions in human SC endothelial cell monolayers, than suppression of individual tight junction proteins. We postulate that the there is an increased and/or synergistic effect when two or more of claudin-11, Tricellulin or ZO-1 are administered together. We have found that the administration of an RNAi inducing agent targeting tight junction proteins claudin-11, Tricellulin and ZO-1 reduces the expression of claudin-11, Tricellulin and ZO-1 mRNA by between 1-fold and 100-fold, preferably 1 to 10 fold, more preferably 1.5 fold to 10 fold when present in a cell at 24, 48 and 72 hours post-transfection.

We have observed time-dependent down-regulation of claudin-11 protein expression at 24, 48 and 72 h post-transfection respectively, as compared to non-targeting (NT) siRNA (FIG. 4a); time-dependent down-regulation of ZO-1 protein expression at 24, 48 and 72 h post-transfection respectively (FIG. 4b); and time-dependent down-regulation of tricellulin protein expression at 24, 48 and 72 h respectively following siRNA treatment (FIG. 4c).

We postulate that any differences in knockdown efficiencies observed indicate that ZO-1 and tricellulin have slower protein turnover rates than claudin-11 in cultured SCEC.

It will be understood that the treatment of the invention results in the reversible, transient, controlled and size selective opening of the tight junction complex joining Schlemm's canal endothelial cells. We have shown these effects are observed up to 48 hours post-adminstration of the RNAi-inducing agent. We postulate that as the effect of the siRNAs is transient, repeated administration will be required to maintain therapeutic efficacy. A preferred mode of delivery, as discussed below is episcleral injection or any other a non-invasive means to deliver the RNAi inducing agent to Schlemm's canal endothelial cells.

It will be understood that the RNAi inducing agent is preferably an RNAi-inducing nucleic acid capable of inhibiting the expression of the tight junction proteins expressed in the tight junction complex of Schlemm's canal at the mRNA level. For example, the RNAi inducing agent may be selected from siRNA, shRNA and an RNAi-inducing vector whose presence within a cell results in production of an siRNA or shRNA, such as a nucleic acid vector encoding an RNAi agent and a virus carrying such vector.

The RNAi inducing agent of the invention is for use in the treatment of glaucoma, including primary or secondary glaucoma.

It will be understood that primary glaucoma covers either the open- or closed-angle form of disease and is not caused by any other observable pathological entity such as eye injury, steroid use, diabetes etc.

It will be understood that secondary glaucoma covers any form of glaucoma in which there is an identifiable cause of increased eye pressure, resulting in optic nerve damage and vision loss. As with primary glaucoma, secondary glaucoma can be of the open-angle or angle-closure type and it can occur in one or both eyes. Secondary glaucoma may be caused by an eye injury, inflammation, certain drugs such as steroids and advanced cases of cataract or diabetes. Examples of secondary glaucoma include exfoliative, neovascular, pigmentary, traumatic, uveitic and congenital glaucoma.

According to a preferred embodiment of the invention, the RNAi inducing agent of the invention is for use in the treatment of open angle glaucoma, preferably primary or secondary open angle glaucoma, more preferably primary open-angle glaucoma (POAG).

We have found that the RNAi inducing agent of the invention reduces transendothelial electrical resistance of SC endothelial cells in-vitro. Advantageously, the RNAi inducing agent of the invention may be used for the reduction of intra-ocular pressure. It will be understood that the RNAi inducing agent of the present invention aims to reduce ocular hypertension (i.e. intra-ocular pressure) by targeting the conventional ocular aqueous humour outflow pathway.

According to a preferred embodiment, the RNAi inducing agent is administered locally to the eye. In this manner the RNAi inducing agent may be administered to target the outflow tissues.

The preferred route of administration is ideally non-invasive or minimally invasive which in the context of the present invention is a 'passive' mode of adminstration. Passive ocular administration routes include, but are not limited to, intracameral or episcleral administration. Alternatively, systemic delivery modes may be contemplated which target the posterior segment of the eye.

According to a preferred embodiment, the RNAi inducing agent may be administered episclerally to the eye, preferably the RNAi inducing agent is administered episclerally into the aqueous humour outflow tissues.

In this manner, the siRNA may be administered into the eye in a retrograde fashion using an episcleral device that attaches to the cornea such that the episcleral veins become more prominent and therefore easier to inject into. A slight pressure is applied to the fluid as it is injected and that enables it to move against the normal flow of fluid from the canal into the episcleral veins from the episcleral veins into Schlemm's canal. In this specification, 'retrograde' involves siRNA delivery into the outflow tissue against the natural flow dynamics of aqueous humour in the anterior chamber. Episcleral delivery of hypertonic solution has previously been demonstrated in rats. Morrison, J. C., Moore, C. G., Deppmeier. L. M. H., Gold, B. G., Meshul, C. K., Johnson, E. C. A rat model of chronic pressure-induced optic nerve damage. Exp. Eye Res. 64, 85-96 (1997). We envisage a similar technique can be used to deliver the RNAi inducing agent of the invention. The aim of such a technique is to make the method as minimally invasive/non-invasive as possible.

The RNAi inducing agent, preferably siRNA or viral vector expressing shRNA (e.g. AAV expressing shRNA), is then injected into an episcleral vein after the device has been placed upon the cornea. It is therefore minimally invasive and less traumatic to a patient.

Alternatively, the RNAi inducing agent, preferably siRNA or viral vector expressing shRNA (e.g. AAV expressing shRNA), may be administered locally to the eye intracamerally, preferably by intracameral injection directly to the anterior chamber. In this manner, injection is directly into the anterior chamber of the eye using a syringe or other means that penetrates the cornea.

The preferred routes of administration are by intracameral inoculation of siRNA, or introduction of siRNA directly into SC endothelium using an episcleral delivery device. These administration routes have the potential of being able to periodically activate virus expressing short hairpin RNAs (shRNA) within SCEC using an inducible promoter. As such, expression of this shRNA could be used as a means of controlling IOP and glaucoma.

Still alternatively, the RNAi inducing agent may be administered by viral mediated delivery of the RNAi inducing agent. For example, the RNAi inducing agent may be an shRNA incorporated into a viral vector, such as an AAV or lentivirus. In this manner, the viral vector is administered by intracameral inoculation into the anterior chamber or episcleral delivery direct to the Schlemm's canal endothelial cells (SCEC).

It will be understood that the administration means generally involve introduction of siRNA into the eye, either in unmodified form, or in combination with other modes of delivery which may include, for example, cationic polymers, modified cationic polymers, peptide molecular transporters, lipids, liposomes, or non-cationic polymers. Alternatively the active agent could be delivered incorporated into a virus—for example AAV, expressing shRNA.

In general, this treatment involves introducing a viral vector comprising the RNAi inducing agent into the anterior chamber of the eye and providing a means for the periodic virally-mediated expression of the RNAi inducing agent. Preferably, the RNAi inducing agent is siRNA or shRNA. For viral mediated delivery, the viral vector will have to transfect Schlemm's canal endothelial cells rather than corneal endothelium.

As described above, there are two avenues of delivery of the viral vector comprising the RNAi inducing agent. The first is by introducing siRNA into the anterior chamber by inoculation or by introducing it by episcleral delivery. The second involves inoculating a virus, for example, an AAV virus into the drainage tissues of the eye. The virus could then be activated periodically by using an activating agent, for example, doxycycline, as an eye drop.

It will be understood that the RNAi inducing agent is administered periodically, as required on the basis of the level of intraocular pressure. For example, the RNAi inducing agent may be administered to a subject daily, weekly or monthly.

According to one embodiment of the invention, the subject is a mammal, preferably a human.

Advantageously, the subject is resistant or non-responsive to conventional pressure lowering medications, such as prostaglandin analogues, Beta blockers, Alpha agonists and/or carbonic anhydrase inhibitors. For example, the subject may have primary open-angle glaucoma (POAG) and does not achieve target IOP when treated with conventional pressure lowering medications. In this situation, the RNAi inducing agent of the present invention provides an alternative or additional therapy.

According to another aspect of the invention, there is provided an ophthalmic solution comprising an RNAi inducing agent targeting the tight junction complex joining Schlemm's canal endothelial cells, optionally with a suitable excipient. For example, the siRNA (RNAi inducing agent) may be supplied in a sterile vial in a lyophilised state. The physician may then re-constitute the siRNA with sterile water or a dilute with buffer.

According a preferred embodiment of this aspect of the invention, the ophthalmic solution comprises an RNAi inducing agent targeting one or more of tight junction proteins claudin-11, Tricellulin, ZO-1, junctional adhesion molecule-3 (JAM-3) or intercellular adhesion molecule-1 (ICAM-1); preferably at least one or more of claudin-11, Tricellulin or ZO-1 or f claudin-11, tricellulin and ZO-1.

Additionally, the ophthalmic solution may be adapted for administration to the eye of the subject in the form of eye droplets. Alternatively, the ophthalmic solution may adapted for intracameral or episcleral administration to the eye. According to another aspect of the invention, there is provided a method for the prevention and/or treatment of glaucoma in a subject comprising the step of administering an effective amount of an RNAi inducing agent capable of reducing and/or inhibiting the expression of one or more tight junction proteins expressed in the tight junction complex joining Schlemm's canal endothelial cells (SCEC) in the eye of the subject. It will be understood that an effective amount of the RNAi-inducing agent is the amount need to down-regulate the tight junction proteins expressed in the tight junction complex joining Schlemm's canal endothelial cells (SCEC) in the eye.

According to one embodiment, the RNAi inducing agent targets one or more of tight junction proteins claudin-11, Tricellulin, ZO-1, junctional adhesion molecule-3 (JAM-3) or intercellular adhesion molecule-1 (ICAM-1); preferably at least one or more of claudin-11, Tricellulin or ZO-1. Additionally, the RNAi inducing agent may targets tight junction proteins claudin-11, tricellulin and ZO-1. In this manner administration of the RNAi inducing agent may be simultaneously or sequentially.

As described above, the RNAi inducing agent is selected from siRNA, shRNA and an RNAi-inducing vector whose presence within a cell results in production of an siRNA or shRNA.

It will be understood that glaucoma may be a primary or secondary glaucoma, preferably open angle glaucoma, preferably primary or secondary open angle glaucoma, more preferably primary open-angle glaucoma (POAG).

Preferably, the RNAi inducing agent is administered locally to the eye. According to one embodiment, the RNAi inducing agent is administered by intracameral injection. According to another embodiment, the RNAi inducing agent is administered episclerally into the aqueous humour outflow tissues.

Ideally, the subject is a mammal, preferably a human. For example, as described above, the subject may be resistant or non-responsive to conventional pressure lowering medications.

According to another aspect of the invention, there is provided a method for reducing intra-ocular pressure comprising administering an effective amount of an RNAi inducing agent targeting the tight junction complex joining Schlemm's canal endothelial cells to a subject in need thereof.

According to yet another aspect of the invention, there is provided a method for treating ocular hypertension comprising administering an effective amount of an RNAi inducing agent targeting the tight junction complex joining Schlemm's canal endothelial cells to a subject in need thereof.

In the specification, the terms "comprise, comprises, comprised and comprising" and any variation thereof and the terms "include, includes, included and including" and any variation thereof are considered to be totally interchangeable and they should all be afforded the widest interpretation. The invention is not limited to the embodiments described above but may be varied within the scope of the claims.

DESCRIPTION OF THE FIGURES

Embodiments of the present invention will now be described, with reference to the accompanying, non-limiting example and figures, in which:

FIG. 2: Characterisation of tight junction expression in human Schlemm's canal endothelial cells. (a) The human TJs RT$^2$ Profiler PCR array was used to profile the expression of claudin and adhesion junctional proteins. Histograms illustrate average relative gene expression ($2^{-\Delta CT}$) normalised to 5 housekeeping genes from 4 different human SCE cell strains. Error bars denote SEM. (b) Protein analysis of claudin-11, ZO-1, tricellulin, VE-cadherin, occludin and claudin-5 in cultured human SCECs. HBMEC=human brain microvascular endothelial cells; BCF=Mouse brain capillary fraction. Different SC strains are denoted followed by passage (P) number. (c) White arrow heads illustrate immunodetection of ZO-1, claudin-11 and tricellulin (Cy3) in cultured human SCECs. Blue=DAPI nuclei staining. Scale bar denotes 50 μm. (d) Comparison of claudin-11 and ZO-1 gene expression between healthy and glaucomatous SCECs. Histograms depict mean fold change ±SEM. (unpaired t-test, n=3 healthy and n=2 glaucomatous SCEC cell strains). (e) Western blots comparing claudin-11 and ZO-1 protein expression between normal (SC80) and glaucomatous (SC64 g) SCECs. Histograms depict densitometric changes in protein expression ±SEM. (unpaired t-test, n=4). (f) TEER was measured in cultured glaucomatous (SC57 g) and healthy (SC68) SCEC monolayers after a 5-day culture period. Error bars, mean±SEM. (unpaired t-test, n=3).

Figure 5:
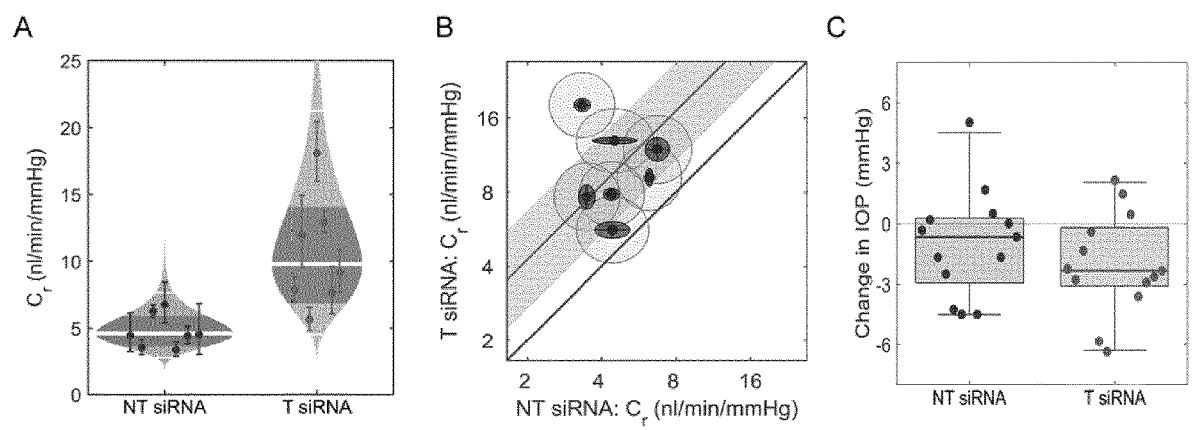

FIG. 5: Effect of down-regulation of tight junction proteins on outflow facility ex vivo (a) 'Cello' plots showing the individual values and statistical distribution of outflow facility at 8 mmHg ($C_r$) for eyes treated with either non-targeting (NT) siRNA or a combination of ZO-1 (SEQ ID NOS:2 and 3) and tricellulin (SEQ ID NOS:8 and 9) targeting (T) siRNA. Each individual point represents a single eye, with error bars showing the 95% confidence intervals on $C_r$ arising from the regression analysis. For each condition, the predicted log-normal distribution is shown, with the thick central white band showing the geometric mean and the thinner white bands showing two geometric standard deviations from the mean. The shaded central region indicates the 95% confidence interval on the mean. (b) Paired facility plot: each data point represents one pair of eyes, with $C_r$ for the treated T siRNA eye on the Y-axis and the $C_r$ for contralateral control NT-siRNA eye on the X-axis. The red line shows the average difference between contralateral eyes, with its confidence interval in grey, whilst the blue line represents the case where the facility would be identical between contralateral eyes. All data points are above the blue unity line, indicating that the facility was higher in the treated eyes compared to the controls; N=7, p=0.006. Inner blue ellipses show the 95% confidence intervals on $C_r$ arising from the regression analysis, whilst the green outer ellipses show additional uncertainty due variability between contralateral eyes, estimated from 10 pairs of C57BL/6 eyes perfused only with glucose supplemented PBS (34). (c) Box plot showing the change in IOP in eyes treated with either NT siRNA or T siRNA. Individual data points indicate the difference in IOP for individual eyes at 48 hours post-injection relative to that immediately before injection. The central band represents the median value, boxes show the interquartile range, and error bars show $5^{th}$ and $95^{th}$ percentiles.

Figure 6:
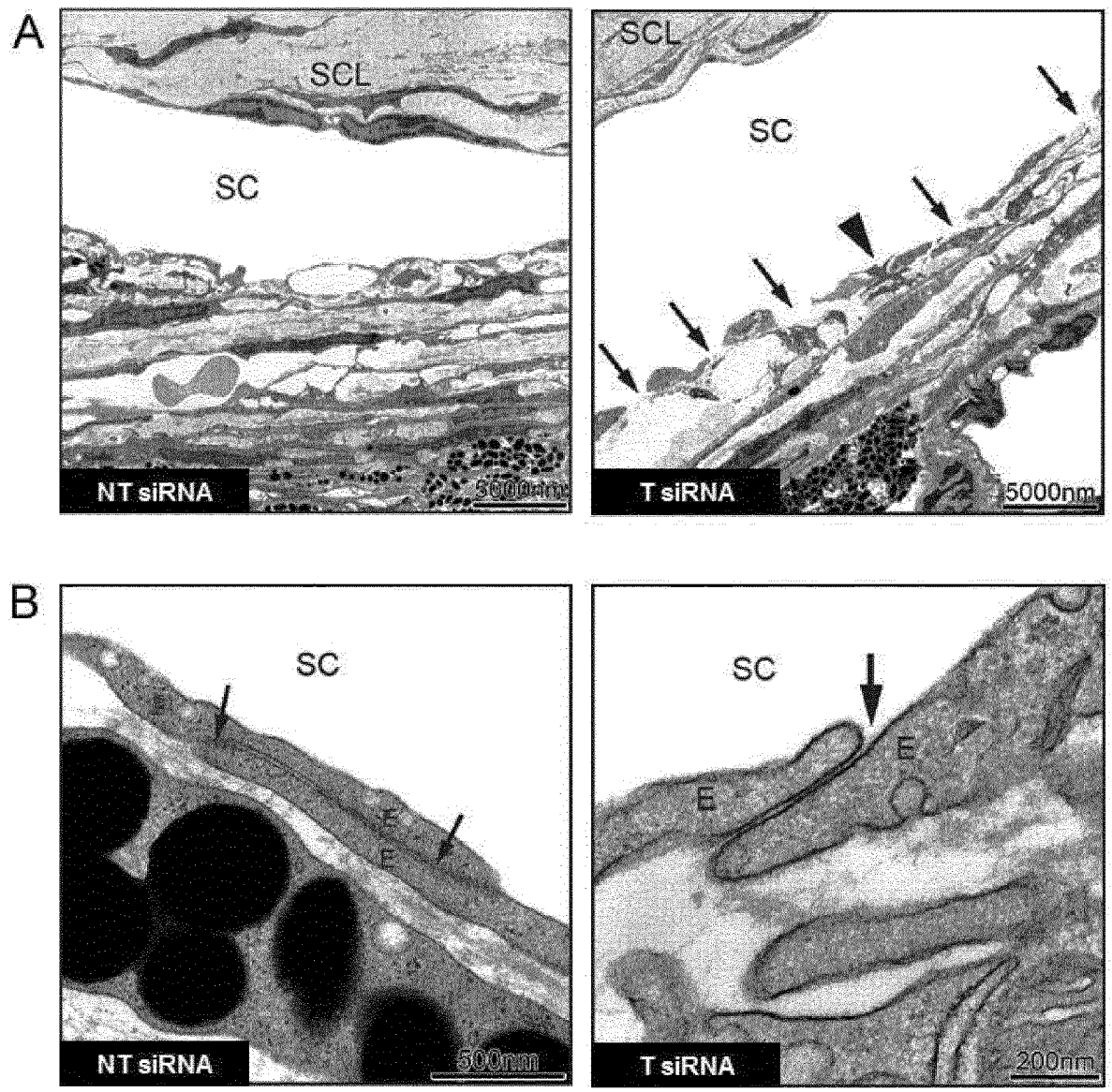

FIG. 6: Transmission electron microscopic analysis of cross section of the inner wall of SC following siRNA-mediated knockdown of tight junction proteins. (a) A representative sagittal section of a mouse eye treated with non-targeting (NT) siRNA illustrating an intact and continuous inner wall endothelium (left panel). In contrast, in the treated eye (T siRNA, right panel G9M1) there are regions of the outflow pathway exhibiting multiple intercellular gaps (small arrows) between inner wall endothelial cells. The bold arrow indicates a sub-endothelial cell filling in the intercellular gap between two endothelial cells. SC=Schlemm canal; SCL=Sclera. In this case, the number and size of endothelial gaps as well as the facility increase were especially high. Scale bar denotes 5000 nm. (b) A sagittal section through an intercellular cleft along the inner wall endothelium of SC in a mouse treated with non-targeting (NT) siRNA illustrates two tight junction strands between neighbouring SCEC (arrows, left panel). In the siRNA treated eye (T siRNA, right panel), the cell membranes of adjacent endothelial cells (E) of the inner wall of SC are not fused as indicated by the arrow, but a clear separation in the entire length of the cell membrane is visible. Scale bars denote 500 nm (left) and 200 nm (right).

Figure 7:
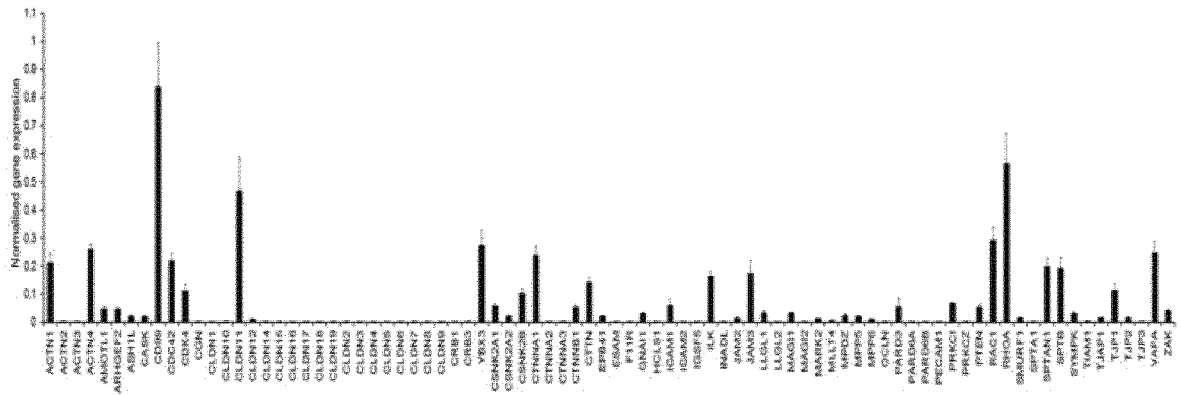

FIG. 7: A complete normalised gene expression pattern of human TJs in cultured human SCECs. SC65, 68, 76 and 77 SCEC strains were used for this study. Error bars, mean±SEM.

Figure 8:
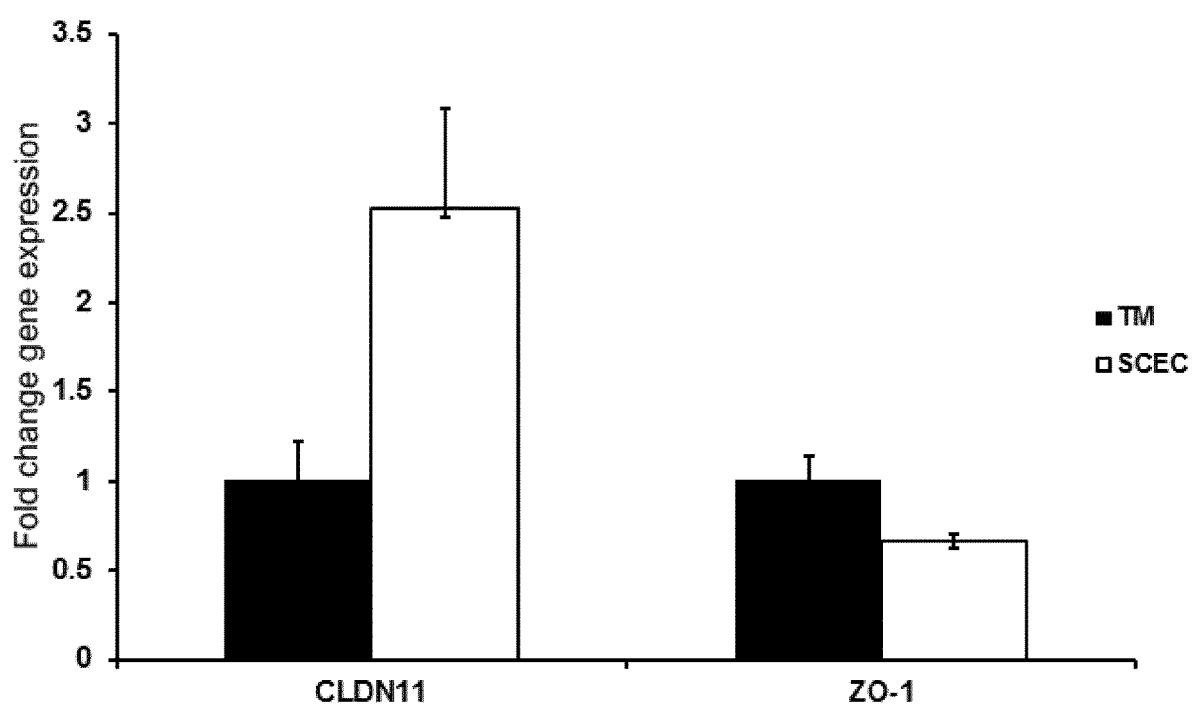

FIG. 8: Comparison of claudin-11 and ZO-1 gene expression between cultured human SCE and TM cells. Fold change in gene expression was determined by the $2^{-\Delta\Delta ct}$ method. Data represent mean fold change of SC77 and TM93 cell strains at two passage numbers.

Figure 9:
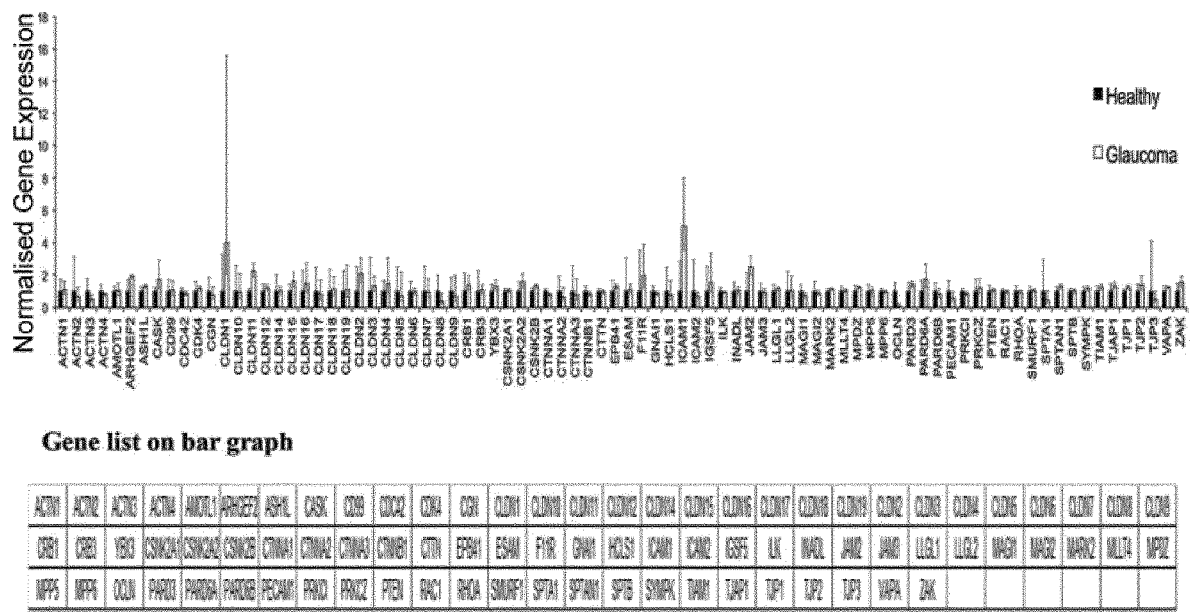

FIG. 9: A complete fold change gene expression pattern of TJs between healthy and glaucomatous SCECs. Data represent mean fold change between healthy (SC68, SC76, SC 77) and glaucomatous (SC 57 g, 63 g, 64 g) SCEC strains. (Note: SC 63 g and 64 g were derived from different eyes of the same donor). Error bars, mean±SEM.

Figure 10:
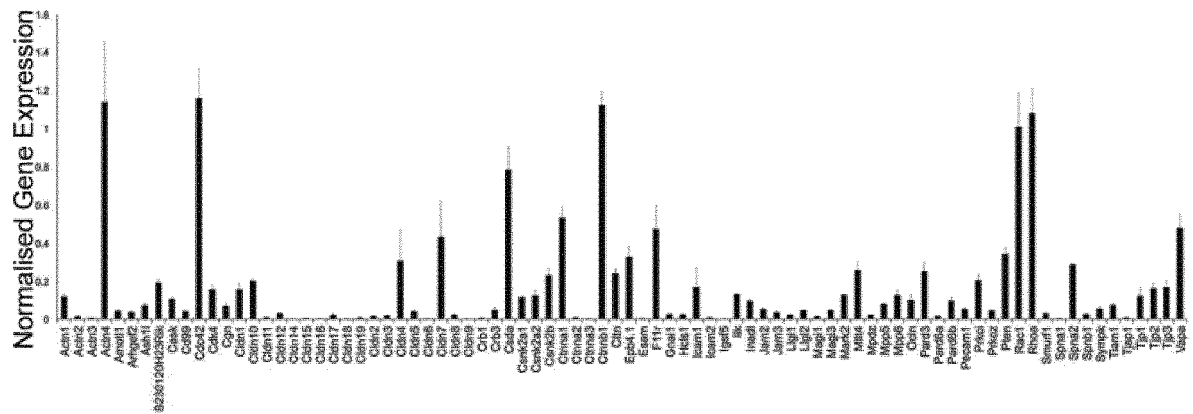

FIG. 10: Representative flow vs. pressure plot for a pair of eyes. Each data point shows the average of 4 minutes of stable flow at each pressure step, and error bars represent two standard deviations. A power-law model (see Methods) is fit to the data and the confidence bounds of the fit are represented by the shaded areas.

Figure 11:
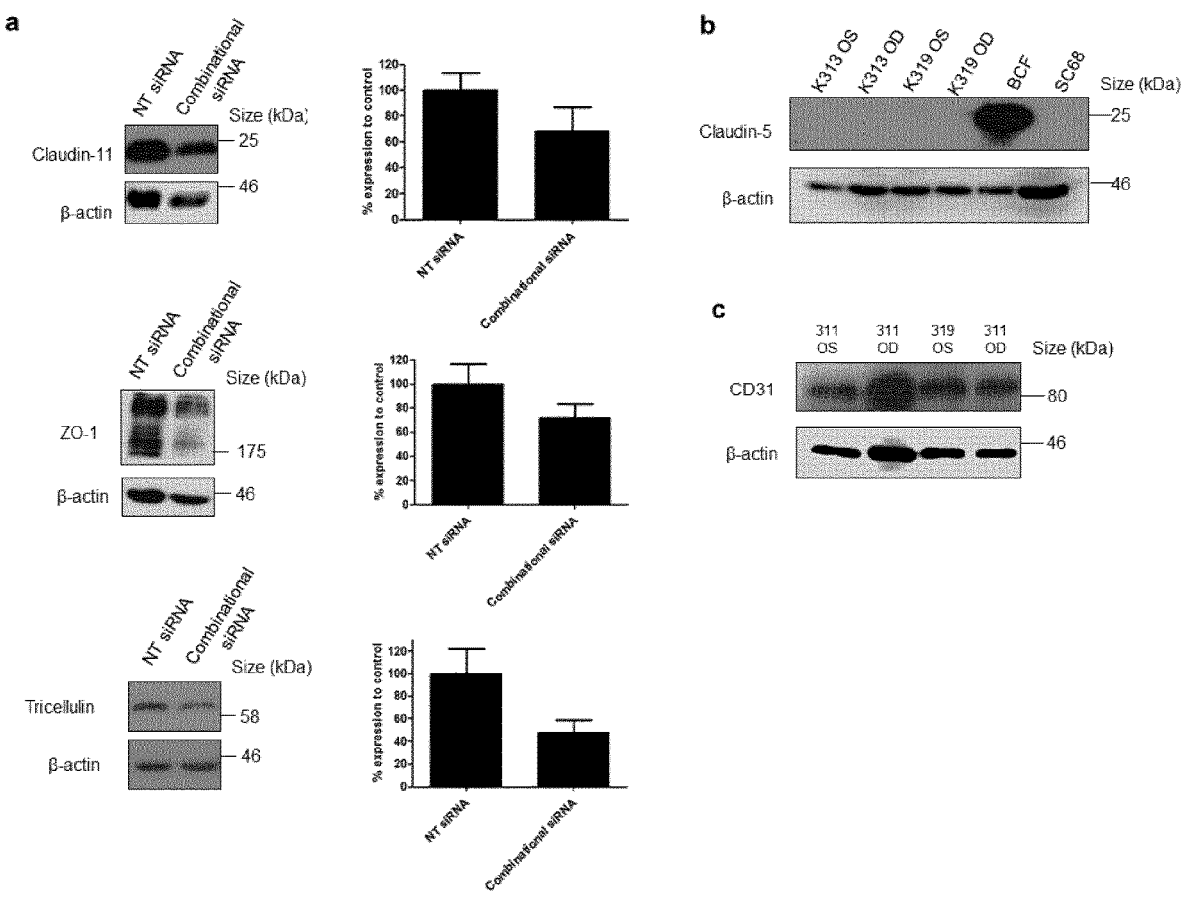

FIG. 11: The distribution of outflow around the circumference of the murine conventional outflow pathway as visualised using fluorescent tracer nanoparticles. C57BL/6 mice were treated with non-targeting siRNA (A) in one eye and targeting siRNA (B) in the contralateral eye following the methods described in the main text. 48 hours after injection, eyes were perfused ex vivo at a constant pressure of 8 mmHg for 10 hours with fluorescent tracer nanoparticles (0.1% v/v, 20 nm; Fluospheres; Invitrogen). The eyes were immersion fixed in 4% paraformaldehyde, and dissected to visualise the distribution of fluorescent tracer around the circumference of the outflow pathway that was imaged using confocal microscopy. The tracer patterns reveal variations in fluorescence intensity around the circumference of the outflow pathway, indicating non-uniform or segmental outflow. Regions of higher tracer fluorescence (white asterisks) would likely experience greater delivery of siRNA and thereby exhibit larger morphological changes relative to regions of lower tracer fluorescence. This may contribute to the variability in gap numbers between different regions of individual eyes reported in Supplemental Table 1. No obvious differences in tracer patterns were observed between eyes treated with targeting and non-targeting siRNA. S, superior quadrant; T, temporal quadrant; I, inferior quadrant; N, nasal quadrant.

Figure 12:
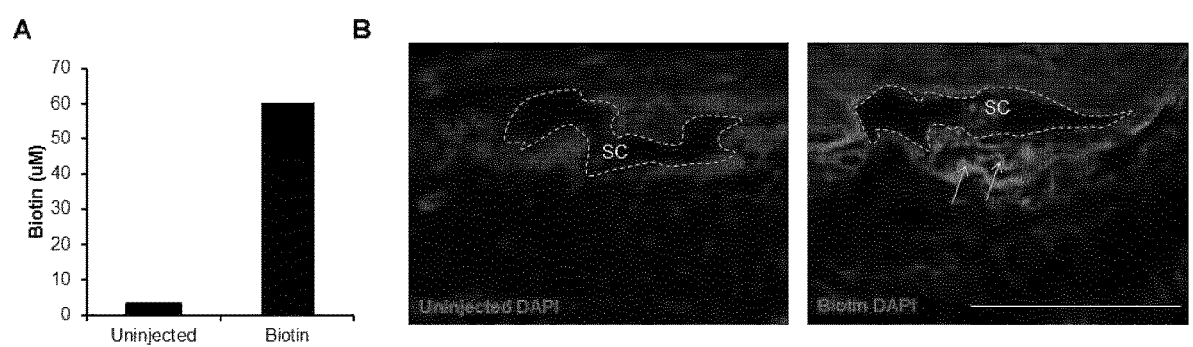

FIG. 12: (a) Quantification of Biotin (µM) following episcleral injection. Aqueous humour was extracted from eyes of three mice 5 min post-injection, pooled, and fluorescent signals were determined. (b) Frozen sections of anterior segments following episcleral delivery of biotin. Scale bar denotes 50 µm. Biotin tracer molecule=red. DAPI=blue. SC=Schlemm's Canal. Arrows indicate detection of biotin in outflow tissues.

EXAMPLES

Example 1

Materials and Methods
Cell Culture

Human SCEC and TM cells were isolated, cultured and characterized as previously described in Stamer W D et al (1995) Isolation and culture of human trabecular meshwork cells by extracellular matrix degradation. Curr Eye Res 14: 611-617 and Stamer W D et al (1998) Isolation, culture and characterization of endothelial cells from Schlemm's Canal. IOVS 39: 1804-1812). SCEC strains used in this study were derived from several patients and denoted SC65, SC68, SC73, SC76, SC77 and SC83. Glaucomatous SCEC strains used were SC57 g, SC63 g, SC64 g, SC69 g (Note: SC63 g and SC64 g were derived from different eyes of the same donor). TM93 was the single TM cell strain used. All SCE and TM cells were used at passages 2-6. SCECs were cultured in low glucose Dulbecco's modified Eagle medium (Gibco, Life Sciences) supplemented with 10% Performance Plus fetal bovine serum (FBS) (Gibco, Life Sciences), 1% Pen/Strep glutamine (Gibco, Life Sciences), in a 5% $CO_2$ incubator at 37° C. TM cells underwent a differentiation step by plating at full confluency for one week in media containing 10% FBS, and changed over to media containing 1% FBS for an additional week prior to experimentation. Cultured cells were passaged with trypsin-EDTA (Gibco-BRL) to maintain exponential growth.

Human Tight Junction PCR Array

The human TJ $RT^2$ Profiler PCR array (PAHS-143ZA, Qiagen) was used to profile the expression of 84 key genes (yes, the identity of these genes are available commercially on Qiagen's website) encoding proteins that form selective barriers between epithelial and endothelial cells to regulate size selectivity, polarity, proliferation and differentiation. Total RNA was extracted from four different human SC cell strains (SC65, 68, 76 and 77) at passages 3 to 5 using RNEasy Mini Kit (Qiagen) according to manufacturer's protocol. Genomic DNA contamination was eliminated by DNase treatment. Total RNA was reverse-transcribed into cDNA using $RT^2$ First Strand Kit (Qiagen). The Threshold cycle (Ct) values of different passage numbers from each SCEC strain were determined and averaged using ABI Prism 7700 Sequence Detector. The mean normalised expression ($2^{-\Delta Ct}$) of genes encoding claudin and adhesion junctional proteins was determined and analysed using the online Qiagen $RT^2$ Profiler PCR Array Data Analysis software. Normalised gene expression was calculated by using the equation: $2^{\Delta Ct} = 2^{-[Ct(gene\ of\ interest) - Ct(Housekeeping\ genes)]}$. Normalisation was carried out with five housekeeping genes (ACTB, B2M, GAPDH, HPRT1 and RPLP0) included in the PCR array. For the comparison of junctional proteins between healthy and glaucomatous SCEC, total RNA was extracted from 3 different healthy (SC68, 76 and 77 at passage 3, respectively) and 2 glaucomatous (SC57 g and SC 63 g/64 g at passage 3, respectively) SCEC strains, and profiled using the human TJ $RT^2$ PCR Profiler PCR array. The $2^{-\Delta\Delta CT} = 2^{-\Delta Ct\ treated}/2^{-\Delta Ct\ control}$ method was used to calculate fold changes for each gene as difference in gene expression (43). A positive value indicates gene up-regulation and a negative value indicates gene down-regulation.

Western Blotting

Protein lysates were isolated from cultured cells in protein lysis buffer containing 1M Tris pH 7.5, 1M NaCl, 1% NP-40, 10% SDS, 1× protease inhibitor cocktail (Roche). The homogenate was centrifuged at 10,000 r.p.m. (IEC Micromax microcentrifuge, 851 rotor) at 4° C. for 20 min and the supernatant was stored at −80° C. Protein concentration was determined by BCA Protein assay kit (Pierce, IL, USA) with bovine serum albumin (BSA) at 2 mg/ml as standards on 96-well plates according to the manufacturer's protocol. 30-50 µg of total protein was loaded in each lane. Protein samples were separated by electrophoresis on 7.5-10% SDS-PAGE under reducing conditions and electrotransferred to PVDF membranes. After blocking with 5% blotting grade blocker non-fat dry milk in TBS for 1 hour at room temperature, membranes were incubated overnight at 4° C. with the following Rabbit polyclonal primary antibodies: anti-oligodendrocyte specific protein antibody (1:500; Abcam); anti-ZO-1 antibody (1:250; Invitrogen), anti-tricellulin C-terminal antibody (1:125; Invitrogen), anti-occludin antibody (1:500, Invitrogen) and anti-VE-cadherin antibody (1:1000; Abcam). Blots were washed with TBS and incubated with horse radish peroxidase-conjugated polyclonal rabbit IgG secondary antibody (Abcam). The blots were developed using enhanced chemiluminescent kit (Pierce Chemical Co.) and exposed to Fuji X-ray films in a dark-room facility. Each blot was stripped with Restore Western Blot Stripping Buffer (Pierce) and probed with rabbit polyclonal to β-actin (Abcam) as loading controls. Protein band intensities were quantified by scanning with a HP Scanjet Professional 10000 Mobile Scanner and analysed using Image J (Version 1.50c). The percentage reduction in band intensity was calculated relative to the control non-targeting siRNA, which was standardised to represent 100% and normalised against β-actin.

Immunostaining

Immunocytochemistry

Human SCEC were grown on Lab-Tek II chamber slides and fixed in 4% paraformaldehyde (pH 7.4) for 15 mins at room temperature and then washed with PBS for 15 mins. Cell monolayers were blocked in PBS containing 5% normal goat serum and 0.1% Triton X-100 at room temperature for 15 mins. Primary antibodies were diluted at 1:100 in blocking buffer and incubated overnight at 4° C. Secondary antibodies diluted at 1:500 were then incubated for 1 hr at 37° C. Following incubation, chamber slides were mounted with aqua-polymount (Polyscience) after nuclei-counterstaining with DAPI. Fluorescent images of SCEC monolayers were captured using a confocal microscope (Zeiss LSM 710), and processed using an imaging software (ZEN 2012).

Immunohistochemistry for Frozen Sections

Enucleated mouse eyes were fixed in 4% paraformaldehyde (pH 7.4) overnight at 4° C. on a rotating device. Posterior segments of the eye were removed and anterior segments were then washed with PBS for 15 mins and sequentially submerged in 10, 20 and 30% sucrose. Dissected anterior segments were then suspended in specimen blocks with OCT solution (Tissue Tek) and frozen in a bath of isopropanol submerged in liquid nitrogen. Frozen anterior segments were sectioned using a cryostat (Leica CM 1900) to 12 µm thickness. Sections were collected on Polysine slides (Menzel-Glazer). To detect TJ proteins, sections were blocked for 20 min at room temperature in PBS containing 5% goat serum and 0.1% Triton-X, and incubated with the corresponding antibodies at 1:100 dilutions overnight at 4° C. in a humidity chamber. All sections were then washed three times in PBS and incubated with Cy-3 labelled anti-rabbit IgG antibody at 1:500 (Abcam) for 1 h at 37° C. in a humidity chamber. Following incubation, sections were washed with PBS and mounted with aqua-polymount (Polyscience) after nuclei-counterstaining with DAPI. Anterior segments were visualized using a confocal microscope (Zeiss LSM 710).

Immunohistochemistry for Paraffin Embedded Sections

Paraffin sections of African green monkey (Chlorocebus Sabeus) anterior segments were rehydrated by immersion in the following solutions: twice for 2 mins each in Histoclear solution; 100% ethanol for 1 min; 95% ethanol for 1 min; 70% ethanol for 1 min; deionised water for 1 min; washing twice for 5 mins in PBS. For antigen retrieval, paraffin sections were heated to 95° C. for 10 min in citrate buffer (Sodium citrate, pH 6). Paraffin sections were then blocked and stained as described above.

siRNAs

All in vivo predesigned siRNAs used in this study were synthesised by Ambion and reconstituted as per manufacturer's protocol. siRNA identification numbers are as follows: human claudin-11 siRNA (5'-gtcatttacttgtacgaga-3'

(SEQ ID NO: 1), ID number: s9925), human ZO-1 siRNA (5'-cgatctcataaacttcgta-3' (SEQ ID NO: 4), ID number: s14156), human MARVELD2 siRNA (5'-ggattagcttggatcacca-3' (SEQ ID NO: 7), ID number: s45794), mouse ZO-1 siRNA (5'-cattcgccttcatacaata-3' (SEQ ID NO: 10), ID number: s75175), mouse MARVELD2 siRNA (5'-acgagagaatttcaagaat-3' (SEQ ID NO: 13), ID number: ADCSU2H) (overhangs in lower case and underlined).

```
human claudin-11 siRNA (5'-gtcatttacttgtacgaga-3'
(SEQ ID NO: 1), ID number: s9925);

(SEQ ID NO: 2)
Sense (5' → 3') GTCATTTACTTGTACGAGAtt (SEQ ID NO: 3)
Antisense (5' → 3') TCTCGTACAAGTAAATGACct human ZO-1 siRNA (5'-cgatctcataaacttcgta-3'
(SEQ ID NO: 4), ID number: s14156);

(SEQ ID NO: 5)
Sense (5' → 3') CGATCTCATAAACTTCGTAtt (SEQ ID NO: 6)
Antisense (5' → 3') TACGAAGTTTATGAGATCGct human MARVELD2 siRNA (5'-ggattagcttggatcacca-3'
(SEQ ID NO: 7), ID number: s45794);

(SEQ ID NO: 8)
Sense (5' → 3') ACGAGAGAATTTCAAGAATtt (SEQ ID NO: 9)
Antisense (5' → 3') ATTCTTGAAATTCTCTCGTtt mouse ZO-1 siRNA (5'-cattcgccttcatacaata-3'
(SEQ ID NO: 10), ID number: s75175;

(SEQ ID NO: 11)
Sense (5' → 3') CATTCGCCTTCATACAATAtt (SEQ ID NO: 12)
Antisense (5' → 3') TATTGTATGAAGGCGAATGat mouse MARVELD2 siRNA (5'-acgagagaatttcaagaat-3'
(SEQ ID NO: 13), ID number: ADCSU2H).

(SEQ ID NO: 14)
Sense (5' → 3') GGATTAGCTTGGATCACCAtt (SEQ ID NO: 15)
Antisense (5' → 3') TGGTGATCCAAGCTAATCCag.
```

Silencer Negative control siRNA (Ambion) was used as a non-targeting control in knockdown studies.

Measurement of SCE Monolayer Transendothelial Electrical Resistance (TEER)

TEER was used as a measure of TJ integrity by the human SCEC monolayers. Human SCEC ($1\times10^4$ cells per well) were grown to confluency on Costar HTS Transwell-polyester membrane inserts with a pore size of 0.4 µm. The volume of the apical side (inside of the membrane inserts) was 0.1 ml and that of the basal side (outside of the membrane inserts) was 0.6 ml. Confluent cells were then transfected in triplicates with 40 nM of claudin-11 (SEQ ID NOS:2 and 3), ZO-1 (SEQ ID NOS:5 and 6) and tricellulin (SEQ ID NOS:8 and 9) siRNAs, or in combination, using Lipofectamine RNAiMax reagent as outlined by the manufacturer (Life Technologies). Non-targeting siRNA was used as a control. 48 hrs post-transfection, TEER values were determined using an EVOM resistance meter with Endohm Chamber (World Precision Instruments) and a Millicell-Electrical Resistance System. For measurement of TEER, both the apical and basolateral sides of the endothelial cells were bathed in fresh growth medium at 37° C., and a current was passed across the monolayer with changes in electrical resistance, which was reported as $\Omega\cdot cm^2$ after correcting for the surface area of the membrane (1.12 cm). Electrical resistance was measured in triplicate wells, and the inherent resistance of a blank transwell was subtracted from the values obtained for the endothelial cells.

Cell Permeability Assay Using FITC-Dextran

Transwell permeability assays were carried out as previously described in (29). In brief, human SCEC were prepared and treated using the same method for TEER measurement as described above. 4 kDa, 10 kDa, 40 kDa, 70 kDa and 150 kDa fluorescein isothiocyanate (FITC)-conjugated dextran (Sigma) was applied at 1 mg/ml to the basal compartment of the Transwells. Sampling aliquots of 0.1 ml were collected every 15 mins for a total of 120 mins from the apical side for fluorescence measurements and the same volume of culturing media was added to replace the medium removed. FITC fluorescence was determined using a spectrofluorometer (Optima Scientific) at an excitation wavelength of 485 nm and an emission wavelength of 520 nm. Relative fluorescence units (RFU) were converted to values of nanograms per millilitre using FITC-dextran standard curves, and were corrected for background fluorescence and serial dilutions over the course of the experiment. The apparent permeability co-efficient ($P_{app}$, cm/s) for each treatment was calculated using the following equation:

$$P_{app}=(dM/dt)/(A\times C_0),$$

where dM/dt (µg/s) is the rate of appearance of FITC-dextran (FD) on the apical side from 0 min to 120 min after application of FD. $C_0$ (µg/ml) is the initial FD concentration on the basal side, and A (cm$^2$) is the effective surface area of the insert. dM/dt is the slope calculated by plotting the cumulative amount of (M) versus time.

Animal Husbandry

The use of animals and injections carried out in this study were in accordance with the European Communities Regulations 2002 and 2005 and the Association for Research in Vision and Ophthalmology statement for the use of Animals in Ophthalmic and Vision Research, and was approved by the institutional Ethics Committee. Male C57BL/6 mice (Charles River Laboratories, UK) of age 10 to 12 weeks were used. Ex vivo perfusions, intracameral injections and IOP measurements were done under the UK Home Office Project License 70/7306 at Imperial College London. Animals were brought into the animal facility one week prior injections for an acclimatization period. Mice were housed in individually ventilated cages with 5 mice per cage. They were provided with food and water ad libitum and were under 12 hr light/dark cycles at 21° C. Animals used for episcleral injection were bred and housed in specific-pathogen free environments in University of Dublin, Trinity College, and was carried out under the HPRA project authorization AE19136/P017.

Intracameral Injection

Adult C57BL/6 mice of 2-3 months of age were anaesthetised by intra-peritoneal injection of domitor and ketamine (1 and 75 µg/g body weight, respectively). Pupils were dilated with 1% cyclopentolate and 2.5% phenylephrine. Glass micro-needles (outer diameter=1 mm, inner diameter=0.58 mm; World Precision Instruments) were pulled using a micropipette puller (Narishige PB-7). Under microscopic control, a pulled blunt-ended micro-glass needle was first used to puncture the cornea to withdraw aqueous humour. Immediately after puncture, a pulled blunt-ended micro-glass needle attached to a 10 µl syringe (Hamilton, Bonaduz, Switzerland) was inserted through the puncture, and 1.5 µl of PBS containing 1 µg of ZO-1 siRNA (SEQ ID NOS:11 and 12) and 1 µg of tricellulin (SEQ ID NOS:14 and 15) siRNA was administered into the anterior chamber to give a final concentration of 16.84 µM. Contraleral eyes received an identical injection of 1.5 µl containing the same concentration of negative control siRNA. Following surgery, a reversing agent (10 µg/g body weight, atipamezole hydrochloride) was delivered by intra-peritoneal injection. Fusidic gel was applied topically to the eye as analgesic and Vidisic gel was also applied topically as a moisturiser and 5 µg/g enrofloxacin antimicrobial (Baytril; Bayer Healthcare, Germany) was injected subcutaneously.

Outflow Facility Measurements 48 hours after siRNA injection, mouse eyes were perfused ex vivo to measure outflow facility using the iPerfusion™ system as described in Sherwood et al. (34). Mice were culled by cervical dislocation and the eyes were enucleated within 5 minutes post mortem and stored in PBS at room temperature to await perfusion. Both eyes were perfused simultaneously using two independent perfusion systems as described previously. Briefly, each eye was affixed to a support using a small amount of cyanoacrylate glue and submerged in a PBS bath regulated at 35° C. The eye was cannulated via the anterior chamber with a 33-gauge beveled needle (NanoFil, #NF33BV-2, World Precision Instruments, US) under a stereomicroscope using a micromanipulator. The iPerfusion system comprises an automated pressure reservoir, a thermal flow sensor (SLG64-0075, Sensirion, Switzerland) and a wet-wet pressure transducer (PX409, Omegadyne, US) in order to apply a desired pressure, measure flow rate out of the system and measure the intraocular pressure respectively. The perfusate was DBG (PBS including divalent cations and 5.5 mM glucose), and was filtered through a 0.22 µm filter (#28145-477, VWR international, UK).

Following cannulation, eyes were perfused for 30 minutes at −8 mmHg to allow the eye to acclimatise to the environment. Subsequently, 9 discrete pressure steps were applied from 4.5 to 21 mmHg, while flow and pressure were recorded. Stability was defined programmatically, and data were averaged over 4 minutes at steady state. A non-linear model was fit to flow-pressure data to account for the pressure dependence of outflow facility in mouse eyes. This model was of the form $Q=C_r P (P/P_r)^\beta$, where Q and P and are the flow rate and pressure respectively, and $C_r$ is the outflow facility at reference pressure $P_r$, which is selected to be 8 mmHg (the approximate physiological pressure drop across the outflow pathway). The power law exponent β quantifies the non-linearity in the Q-P response and thus the pressure dependence of outflow facility. The data analysis methodology described by Sherwood et al. (34) was applied in order to analyse the treatment effect, whilst accounting for measurement uncertainties and statistical significance was evaluated using the paired weighted t-test described therein.

IOP Measurements

IOP measurements were carried out immediately prior to siRNA injection and 48 h after injection using rebound tonometry (TonoLab, Icare, Finland) under general anaesthesia with isoflurane (4%+1 l/min oxygen). All IOP measurements were done between 5 and 7 µm to avoid circadian changes. In order to improve the accuracy of the IOP measurements, the following protocol was developed. Under general anaesthesia, the spontaneous IOP declines steadily and so IOP values should be compared at an equivalent time point relative to the onset of anaesthesia. For each animal, IOP was measured in one eye approximately 3 minutes after the flow of isoflurane commenced. The contralateral eye was measured 1 minute later, and this was repeated three times yielding three IOP measurements, two minutes apart for each eye. In order to optimise accuracy, 5 IOP measurements (each involving 5 rebound events) were acquired at each time point. The TonoLab has a minimum measureable pressure of 7 mmHg, below which 7 mmHg is still output by the device. Hence, it was necessary to use a non-parametric approach to the analysis. The median of the 5 IOP measurements at each time point was calculated and a straight line was fit to the median values at the three time points. The IOP 5 minutes after onset of anaesthesia was then estimated by interpolation. Although this approach may show bias towards overestimating IOP when the measured values go below 7 mmHg over the measurement period, this is conservative with regards to investigating the hypothesised IOP lowering effect of the siRNA treatment. The non-parametric Wilcoxon signed-rank test was used to investigate whether the IOP changed between pre- and post-injection measurements in each eye Transmission Electron Microscopy (TEM)

All eyes were immersion fixed in paraformaldehyde initially and post-fixed in Ito's solution. The eyes were embedded in Epon and semi-thin sagittal sections were cut through the whole globe. Ultrathin sections of SC and TM were cut sagitally from one side of the eye first, and then another ultrathin section approximately 1 mm deeper was cut. If possible, this section was taken from the other side of the eye. In the small mouse eye, this process could be repeated four times. In this way, different parts of the circumference of the eye were evaluated. In ultrathin sections of the entire anterior posterior length of the inner wall, intercellular gaps were counted at magnifications of 7000×. The ultrastructure of the intercellular cleft and TJs between neighbouring SCEC were examined at 50000 or 80000×.

Statistical Analysis

For real-time PCR, TEER and paracellular permeability measurements, Student's t-tests and ANOVA with Bonferroni post-test were carried out using GraphPad Prism 5.0. For ex vivo perfusions, a paired weighted t-test was performed using MATLAB as described in (34). For IOP measurements, the Wilcoxon signed rank test was utilised using MATLAB. Statistical significance was indicated by p ≤0.05.

Episcleral Injection

A detailed protocol is described by Morrison and colleagues (40). In brief, adult C57BL/6 mice were anaesthetised as described above. The centre of a punctured latex sheet was then carefully placed around the globe for 10 mins to isolate episcleral veins. Under microscopic control, a pulled and bevelled micro-glass needle (outer diameter <1 mm; World Precision Instruments) was inserted into the superior episcleral vein, and delivery of EZ-Link Sulfo-NHS-SS-Biotin tracer molecules (Thermo Scientific) was assisted by an infusion pump at the rate of 20 µl/min, with a target volume of 20 µl. 5 mins post-injection, aqueous humour was extracted from the anterior chambers of three animals using a blunt end micro-glass needle, pooled, and fluorescent signals were determined using a spectrofluorometer (Optima Scientific). Following aqueous humour extraction, all animals were sacrificed and eyes were taken for histological analysis.

Results

Characterisation of Tight Junctions in Human SC Endothelial Cells

We examined the TJ expression profile in primary cultures of human SC endothelial cells isolated from four individual donors, with the objective of determining key junctional components that regulate permeability and selectivity of the inner wall of SC. The mean normalised expression ($2^{-\Delta Ct}$) of genes encoding claudin and adhesion junctional proteins from four different SCEC strains is illustrated in FIG. 2a (the complete expression pattern can be found as FIG. 7). As shown in FIG. 2a, claudin-11 (oligodenodrocyte-specific protein) was amongst the highest expressed claudin-based TJ protein in cultured SCEC. In addition, zonula-occludens-1 protein (ZO-1, also known as TJP1), a key component of junctional complexes that regulate TJ formation, was also expressed at high levels in cultured SCEC. The cell-cell adhesion molecule, junctional adhesion molecule-3 (JAM3) was also highly expressed in human SCE cell monolayers. In contrast, occludin and claudin-5, which are major TJ components of human and mouse brain and inner retinal vascular endothelial cells, were expressed at low levels in human SC endothelia. Collectively, these data indicate that claudin-11 is the dominant claudin in the TJs of cultured SCEC, and that ZO-1 is a major junctional associated protein of cultured SCECs. We also compared transcript levels of claudin-11 and ZO-1 in cultured monolayers of SCECs (SC77) against those of TM cells (TM93), and observed expression levels of claudin-11 to be 2.52-fold higher in SCEC than in TM cells (FIG. 8). However, no significant difference in ZO-1 transcript expression was observed between SCE and TM cells.

Claudin-11 and ZO-1 protein expression was detected in cultured human SCECs by Western blot analyses (FIG. 2b). In addition, we detected the expression of another TJ protein, tricellulin (also known as MARVELD2) in cultured SCECs, which was not included in the original PCR array. Consistent with a previous study (30), expression of vascular endothelial (VE)-cadherin was also identified in cultured SCECs. However, we did not detect claudin-5 protein expression in cultured SCEC, and only low levels of occludin expression was detected, an observation consistent with the PCR array in FIG. 2a. In order to examine the expression pattern of TJ proteins in confluent SCEC monolayers, an immunohistochemical (IHC) study was performed. We observed discontinuous membrane-specific staining patterns for claudin-11, ZO-1 and tricellulin in cultured SCEC monolayers (FIG. 2c).

Comparison of Tight Iunction Expression Between Healthy and Glaucomatous Human SCEC We compared expression of key junctional components between healthy and glaucomatous SCEC using the human TJ PCR array. Claudin-11 and ZO-1 expression were up-regulated 2.25-fold (p=0.0005) and 1.23-fold (p=0.03), respectively, in glaucomatous SCECs as compared to healthy SCECs (FIG. 2d) (the complete fold-change expression pattern can be found as FIG. 9). Protein lysates extracted from glaucomatous SCEC also showed greater claudin-11 (p=0.04) and ZO-1 (p=0.04) protein expression than healthy SCEC (FIG. 2e). Furthermore, a glaucomatous SCEC monolayer (SC57 g) exhibited a higher TEER (16±0.14 $\Omega \cdot cm^2$; mean±standard error of mean, SEM, p<0.0001) than a healthy SCEC monolayer (SC68) (14±0.09 $\Omega \cdot cm^2$) after a 5 day culture period (FIG. 2f). These data suggest that an increase in claudin-11 and ZO-1 expression found in glaucomatous SCECs may lead to altered barrier function in the conventional outflow pathway of glaucoma patients and contributes to increased outflow resistance.

Figure 1:
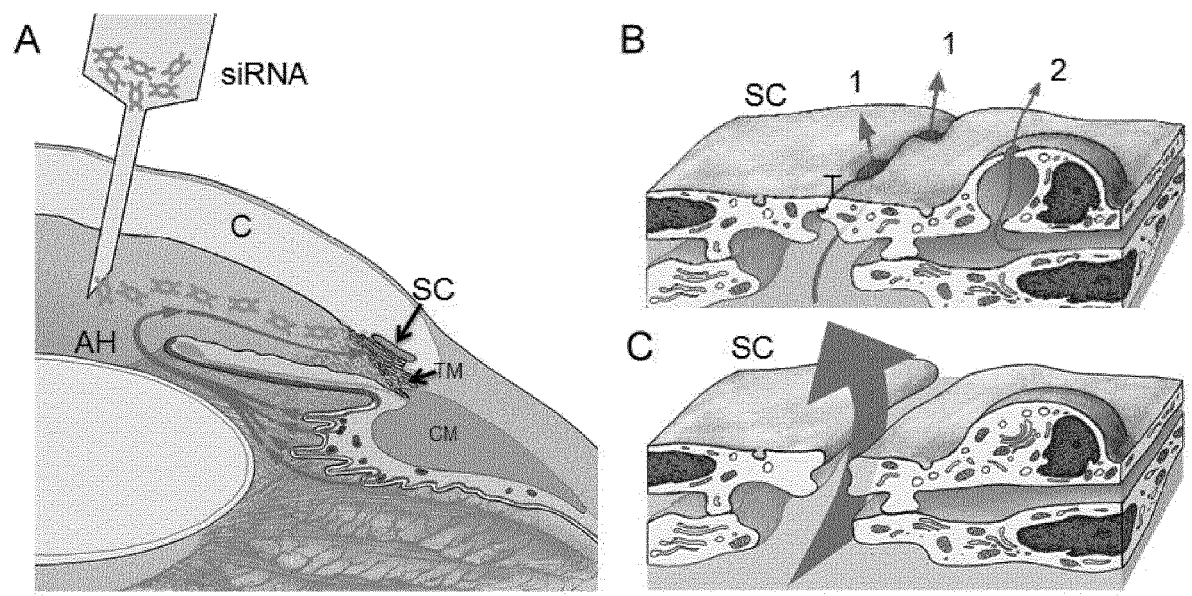
FIG. 1: Schematic illustration of the therapeutic strategy addressed in this study. (a) Intracameral delivery enables siRNAs to be transported towards the conventional outflow pathway by following the natural flow dynamics of aqueous humour in the anterior chamber. AH=aqueous humour; C=cornea; CM=ciliary muscle; SC=Schlemm' canal; TM=trabecular meshwork. (b) Aqueous humour crosses the inner wall endothelium of SC via 1) the intercellular pathway through gaps in tight junctions (T) and, or via 2) the intracellular pathway through a giant vacuole with pore. (c) siRNAs taken up by endothelial cells of the inner wall of SC elicit knockdown of tight junction proteins, resulting in the opening of intercellular clefts with concomitant increase in aqueous outflow facility.
Figure 3:
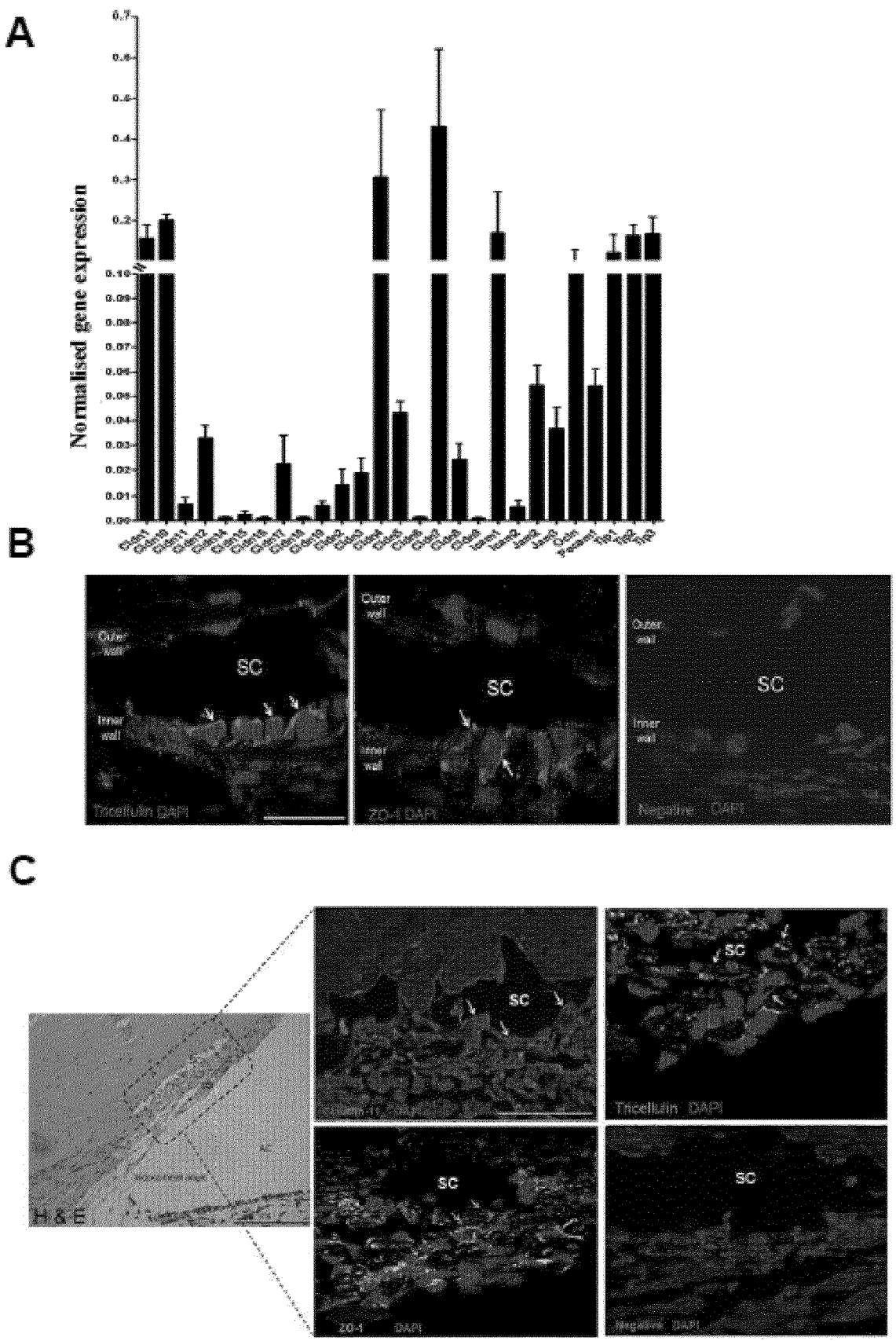
FIG. 3: Characterisation of tight junction expression in mouse and non-human primate outflow tissues. (a) Immunostaining of tricellulin and ZO-1 in frozen sections of mouse anterior segments. ZO-1 and tricellulin=Cy3 (red); DAPI=blue; SC=Schlemm's Canal (b) H & E staining of paraffin monkey anterior segments. AC=anterior chamber; SC=Schlemm's canal; TM=trabecular meshwork. Scale bar denotes 20 μm. Boxed area depicts area shown in immunofluorescent images. Immunofluorescent images of claudin-11, ZO-1 and tricellulin staining in the inner wall endothelium of SC. White arrows indicate detection of corresponding tight junctions at the inner wall of SC endothelium. Scale bar denotes 50 μm.

Characterisation of Expression of Tight Junction and Tight Junction Associated Components in Mouse and Non-Human Primate Outflow Tissues We performed immunohistochemistry (IHC) on frozen sections of mouse anterior segments to localise the expression of TJ proteins in the outflow region comprising TM and the inner wall of SC. FIG. 3a shows tricellulin and ZO-1 staining predominantly localising in the inner wall endothelium of SC. In regions where part of the endothelium was cut oblique to the inner wall of SC, continuous junctional strands were displayed around SCEC margins. ZO-1 and tricellulin staining were also detected in the TM region and in the outer wall. In both regions the endothelial cells are connected by TJs. However, we did not detect claudin-11 or claudin-5 staining in the inner wall of SC and TM with the antibodies used in this study (data not shown). These data indicate that murine outflow tissues may possess a different junctional composition at the inner wall of SC as compared to humans, with the possible absence of claudin-based tight junctional proteins in TM and SC endothelial cells. However, the presence of ZO-1 and tricellulin along the inner wall of mice indicates that these proteins may be suitable targets for assessment of effects of downregulation of TJs in mice.

IHC was performed on paraffin sections of African green monkey anterior segments to identify the junctional composition of the outflow region. Hematoxylin and eosin staining of the anterior chamber clearly identified the iridocorneal angle and conventional outflow tissues (FIG. 3b). Superimposed immunofluorescent imaging showed strong continuous claudin-11 staining along the endothelial cell margins of the inner wall of SC, highly indicative of TJ barrier function (FIG. 3b). Claudin-11 immunostaining was also present along the outer wall of SC and between TM cells. Similarly, ZO-1 and tricellulin staining were also observed in the inner wall endothelium of SC. All three TJ proteins were also present between TM endothelial cells, but the staining was less intense than in the inner wall endothelium. Collectively, these data indicate that SCECs in non-human primates and mice possess a similar TJ barrier composition to those found in humans.

Validation of Tight Junction siRNAs In Vitro

Figure 4:
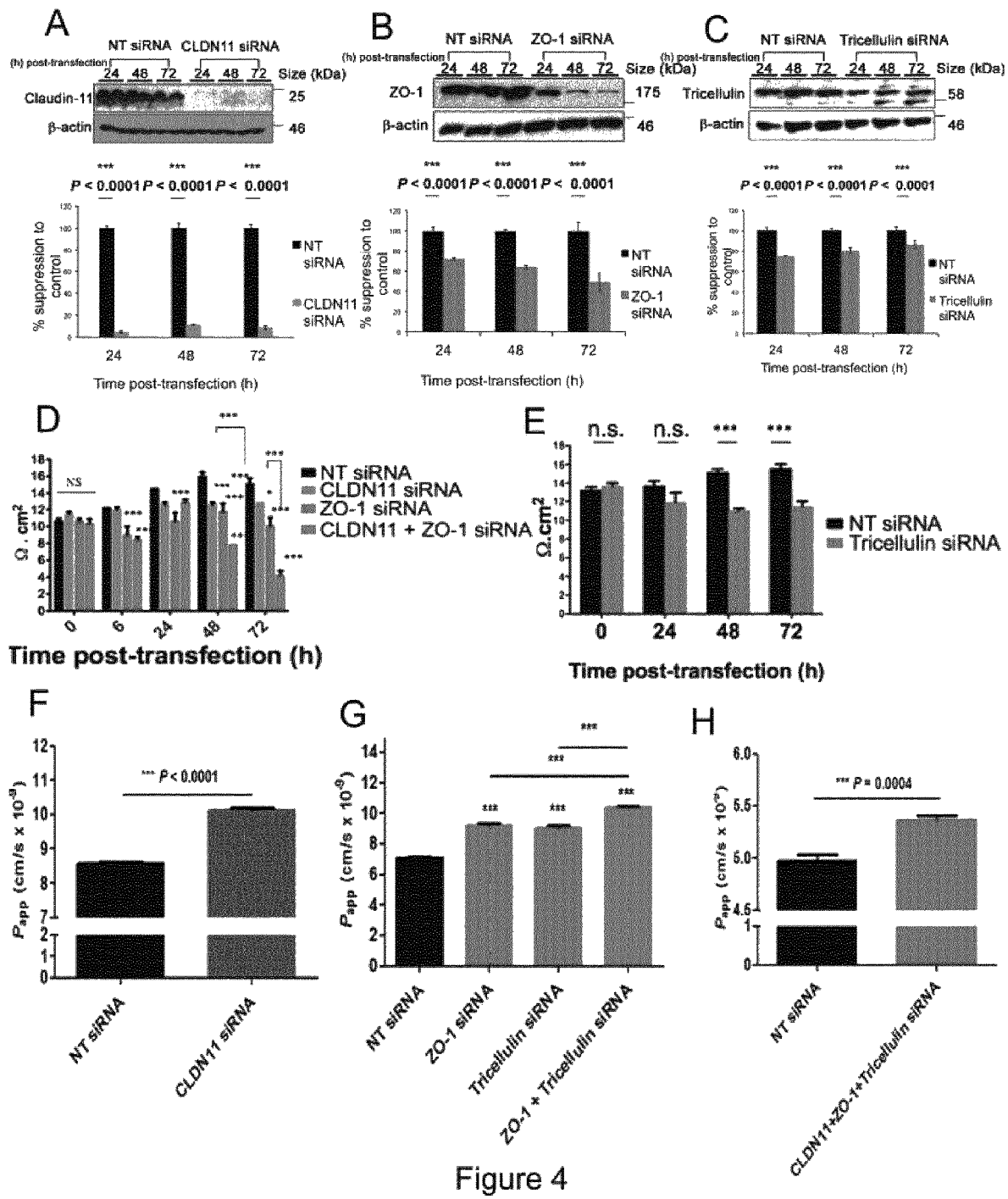
FIG. 4: siRNA-mediated down-regulation of tight junction proteins modulate TEER and paracellular permeability in cultured SCEC monolayers. Representative Western blots of (a) claudin-11, (b) ZO-1 and (c) tricellulin protein knockdown in cultured human SCECs over a 72 h period. Accompanying histograms depict densitometric analysis of percentage protein knockdown normalised to β-actin. NT siRNA=non-targeting siRNA. Error bars, mean±SEM; n.s., non-significant (n=4, unpaired t-test). (d) Effect of siRNA-mediated knockdown of TJ proteins on TEER across human SCEC monolayers. 40 nM of siRNA targeting claudin-11 (SEQ ID NOS:2 and 3), ZO-1 (SEQ ID NOS:5 and 6), or in combination were transfected into human SCECs, and TEER was measured 6, 24, 48 and 72 hours post-transfection. * P<0.05, * P<0.001, n.s. P >0.05 (n=3 separate cell transfection, two way analysis of variance (ANOVA) followed by Bonferroni's multiple comparison post-tests). Error bars, mean±SEM. (e) TEER measurements following treatment with tricellulin siRNAs (SEQ ID NOS:8 and 9) in cultured SCEC monolayer. (n=3 separate cell transfection, two way ANOVA followed by Bonferroni's multiple comparison post-tests). * P<0.0001. Error bars, mean±SEM. (f) Apparent permeability co-efficient ($P_{app}$, cm/s×$10^{-7}$) of 70 kDa FITC-dextran through human SCEC monolayers following treatment with claudin-11 (SEQ ID NOS:2 and 3), ZO-1 (SEQ ID NOS:5 and 6) and tricellulin (SEQ ID NOS:8 and 9) siRNAs, or in combination. NT=non-targeting. Error bars, means±SEM. (middle panel, *** P<0.001) (unpaired Student's t-test; one way ANOVA followed by Bonferroni's post hoc test for multiple comparisons).

In order to validate the suppression efficiency of pre-designed siRNAs targeting the human transcripts of claudin-11, ZO-1 and tricellulin, cultured SCEC were separately transfected with 40 nM of each siRNA, and levels of endogenous TJ protein expression were assessed in a time-dependent manner by Western blot analysis. Time-dependent down-regulation of claudin-11 protein expression to 5±3% (p<0.0001), 11±1% (p<0.0001) and 9±4% (p<0.0001) (mean±SEM), was achieved at 24, 48 and 72 hours post-transfection respectively, as compared to non-targeting (NT) siRNA (N=3, FIG. 4a). ZO-1 protein expression was reduced to 72±3% (p=0.005), 64±4% (p=0.0004) and 49±18% (p=0.02) at 24, 48 and 72 hours post-transfection respectively (FIG. 4b). Furthermore, tricellulin protein expression was reduced to 75±0.2% (p=0.002), 81±6% (p=0.012) and 87±8% (p>0.05, not significant) at 24, 48 and 72 hours respectively following siRNA treatment (FIG. 4c). The difference in knockdown efficiencies likely indicates that ZO-1 and tricellulin have slower protein turnover rates than claudin-11 in cultured SCEC.

Effect of Down-Regulation of Tight-Junctions on SCE Cell Monolayer Permeability

In order to address the hypothesis that down-regulation of TJ components in endothelial cells of SC could be used as a means of modulating the permeability of SC inner wall, TEER assays were used to measure changes in endothelial barrier function in SCEC monolayers following TJ knockdown. FIG. 4d shows that SCECs transfected with claudin-11 (SEQ ID NOS:2 and 3) or ZO-1 (SEQ ID NOS:5 and 6) siRNAs had significantly reduced TEER compared to control siRNAs at 48 and 72 hours post-transfection (p<0.001). Furthermore, transfection with a combination of claudin-11 (SEQ ID NOS:2 and 3) and ZO-1 (SEQ ID NOS:5 and 6) siRNAs also elicited a decrease in TEER, and the level of decrease was more profound than those treated with single siRNAs at 48 and 72 hours post-transfection (p<0.001). Similarly, treatment with tricellulin (SEQ ID NOS:8 and 9) siRNA alone also showed significant reduction of TEER at 48 hours post-transfection, and the effect was sustained up to 72 hours (p<0.001, FIG. 4e).

We sought to determine whether siRNA-mediated downregulation of claudin-11, ZO-1 and tricellulin could increase paracellular permeability in SCEC monolayers. To investigate the size selectivity of paracellular permeability in SCEC monolayer, the flux of 4 kDa, 40 kDa and 70 kDa FITC-dextran (FD) in the basal to apical direction was measured following treatment with claudin-11, ZO-1 or tricellulin siRNAs. At 24 hours post-transfection, a significant increase in paracellular flux of FD, as measured by apparent permeability co-efficient ($P_{app}$), was observed for 70 kDa FITC-dextran following treatment with claudin-11 (p<0.0001), ZO-1 (p<0.001) and tricellulin (p<0.001) siRNAs (FIG. 4f). In particular, $P_{app}$ (70 kDa FD) was observed to be significantly higher in SCEC treated with a combination of ZO-1 (SEQ ID NOS:5 and 6) and tricellulin (SEQ ID NOS:8 and 9) siRNAs than control (p<0.001), and those treated singly with ZO-1 (SEQ ID NOS:5 and 6) or tricellulin (SEQ ID NOS:8 and 9) siRNA (N=4; p<0.001). Furthermore, treatment with a combination of three siRNAs simultaneously also increased $P_{app}$ of SCEC to 70 kDa FD (N=8; p=0.0007 vs control). In contrast, no significant difference was observed in the $P_{app}$ of lower molecular sized FD (4 and 40 kDa) in SCEC monolayers following siRNA treatment (data not shown). Collectively, these data demonstrate that claudin-11, ZO-1 and tricellulin contribute to the barrier function of cultured human SCEC, and that siRNA-mediated down-regulation of these cellular junctional proteins significantly alters endothelial cell barrier integrity and permeability.

Effect of Down-Regulation of Tight Junctions on Outflow Facility and IOP in Mouse Eyes In order to evaluate whether down-regulation of TJs in mice increases outflow facility, studies were performed in mouse eyes because the conventional outflow pathway of mice resembles that of primates morphologically, physiologically and pharmacologically (31-33). We targeted ZO-1 and tricellulin based on the immunohistochemical data in FIG. 3a. Seven wild type C57BL/6 mice were intracamerally injected with a combination of 1 µg ZO-1 siRNA and 1 µg of tricellulin siRNA, and contralateral eyes were injected with 2 µg of NT siRNA. 48 hours post-injection, all animals were sacrificed and enucleated eyes were perfused in pairs using the iPerfusion system (34) to measure outflow facility based on the flow versus pressure relationship acquired over multiple pressure steps (FIG. 10). Outflow facility in the siRNA treated eyes was increased compared to eyes receiving NT siRNA (FIG. 5a). FIG. 5b shows the paired facility data where the facility of the treated eye is plotted against the facility of the contralateral control eye that received NT siRNA, and the treated facility was elevated in all cases (N=7), exhibiting an average facility increase of 113% (confidence interval [35, 234]%, p=0.0064). These data demonstrate that downregulation of TJ components within the conventional outflow pathway significantly increases conventional outflow facility ex vivo.

To determine whether the ex vivo facility increase translates to an in vivo reduction in IOP, we assessed IOP in living mice following knockdown of TJ proteins. Animals were injected with the same concentration of siRNAs as described above. IOP measurements were carried out by rebound tonometry under isoflurane anaesthesia, with measurements taken immediately prior to injection and at 48 hours post-injection. In eyes injected with targeting siRNA, IOP was reduced by 2.3±1.9 mmHg (median±MAD, N=13, p=0.013, Wilcoxon signed-rank test with the null hypothesis of zero average IOP change) compared to pre-injection values. In contrast, IOP was not significantly affected (0.7±1.7 mmHg, p=0.151) in eyes injected with NT siRNA. When comparing the IOP reduction between fellow eyes, targeting siRNA reduced IOP by 1.3±2.7 mmHg more than NT siRNA, but the differences in the IOP change between fellow eyes failed to reach statistical significance (p=0.191, Wilcoxon signed-rank test). This may be attributable to the relatively large variability in IOP measurements combined with a relatively small IOP change in normotensive animals. Nevertheless, the significant increase in outflow facility observed ex vivo in response to targeted siRNA is consistent with IOP reduction measured in treated eyes, and suggests that siRNA-mediated knockdown of TJ proteins may be used to improve outflow by disrupting the continuity of the inner wall endothelium of SC.

Ultrastructural Analysis of the Inner Wall Endothelium of SC Following Knockdown of Tight Junction Proteins To examine how siRNA treatment affects the continuity of the inner wall of SC, ultrastructural investigation was performed by TEM in three pairs of mouse eyes following the ocular perfusion measurements described above. Morphological changes in the inner wall endothelium were most evident in a treated eye that showed the greatest increase in outflow facility (control eye, 4.7 nl/min/mmHg; treated eye, 23.2 nl/min/mmHg). In this case, a large number of endothelial gaps were observed in 3 of 4 independently sampled regions of the treated eye, as compared to the control (FIG. 6a). The cell membranes of the endothelial cells bounding the gaps remained intact, indicating that the gaps likely represented widened intercellular clefts rather than damaged openings through the endothelium. The regional variability in the size and number of endothelial gaps may reflect the regional or 'segmental' variability in the distribution of outflow drainage along the circumference of the outflow pathway (FIG. 10). In the two other cases that had a less pronounced facility increase, endothelial gaps were still observed in the treated eye compared to the control, but the gaps were smaller and fewer compared of the case with the larger facility increase.

To avoid potential artefacts associated with ex vivo manipulation of outflow tissues, we performed ultrastructural analysis of eyes that were not subjected to ocular perfusion. In the three pairs of eyes that were immersion fixed immediately after IOP measurements without iPerfusion, we did not detect endothelial gaps along the inner wall endothelium of SC. Instead, we noted disconnection between the plasma membranes on either side of the intercellular clefts in eyes treated with targeting siRNAs, indicating an absence or weakening of the TJ complexes (FIG. 6b). In the control eyes, the plasma membranes of neighbouring cells were fused at points along the intercellular clefts, indicating an uninterrupted functional TJ. These data indicate that siRNA treatment weakens TJs, allowing the intercellular cleft to expand and form endothelial gaps in response to biomechanical load or stretch acting on the endothelium. As such loads are generated by the basal-to-apical directed pressure drop across the inner wall endothelium, enucleated eyes that were perfused at pressures up to 20 mmHg experienced greater loads, which likely contributed to more endothelial gaps, compared to eyes that were immersion fixed at spontaneous IOP where the pressure drop across the outflow pathway was ~7 mmHg.

Discussion:

Increased outflow resistance through the conventional aqueous humor outflow pathway is the main cause of IOP elevation in POAG. However, despite extensive investigation, the precise pathological mechanism associated with increased outflow resistance has not yet been fully deciphered. As a result, current major treatments for glaucoma have focused largely on inhibiting aqueous production, or increasing unconventional outflow, but have failed to tackle the central pathology of ocular hypertension, namely the mechanism of increased outflow resistance. Hence, there is a clear need to develop novel therapeutics that act to reduce outflow resistance by targeting cells in the conventional outflow pathway with the hope of a better clinical outcome in glaucoma patients.

Aqueous humour exiting the anterior chamber via the conventional outflow pathway passes through the tissues of the TM and into the SC lumen by crossing its endothelial barrier. Conceptually, loosening the TJs known to bind endothelial cells may render the barrier more permeable, in a manner similar to that which has been rigorously established for controlling permeability at the blood-brain and inner blood-retina barriers (27, 28). However, this approach has not been previously assessed in regards to aqueous humour outflow. The current study focused on identifying TJ components present in human, murine and non-human primate outflow tissues that might serve as plausible targets for siRNA-mediated downregulation. A number of such targets were identified in primary cultures of human SCECs, disruption of which has previously been associated with altering endothelial cell permeability in other cell systems (35-37). In particular, glaucomatous SCECs show significantly increased claudin-11 and ZO-1 expression compared to those derived from healthy patients. This indicates that modified barrier function of the inner wall endothelium of SC is a contributing factor to the glaucomatous increase in outflow resistance, possibly by inhibiting or reducing paracellular pore formation along the inner wall. We also revealed that TJ barriers are formed and localised along the endothelial cells of the inner wall of SC in vivo. It is therefore reasonable to speculate, in conjunction with the in vitro permeability assays, that the TJs identified in the inner wall endothelium of SC play a pivotal role in contributing to paracellular movement of aqueous humour and solutes across the endothelial layer. Most importantly, we showed that knockdown of transcripts encoding TJs in the conventional outflow pathway increased aqueous humour outflow facility and lowered IOP in wild type mice, and that this effect is associated with the presence of an increased number of intercellular clefts between SCEC. The larger number and size of intercellular clefts seen in eyes with facility measurements against those without such measurements may be due to supra-physiological pressure drop imposed on the inner wall during intracameral perfusion that acts to enlarge intercellular clefts that have been weakened by knockdown of TJ proteins. It is therefore likely that under escalating pressure conditions, knockdown of TJ proteins would further lower outflow resistance by enabling numerous intercellular gaps to form between neighbouring SCEC. This may have significant implication in the treatment of glaucoma in which the high IOP in glaucomatous eyes may enhance the increase in outflow facility following our therapeutic approach.

While conventional adeno-associated viruses (AAV) have been shown to be inefficient in transducing cells of the outflow tissues, self-complementary AAV have been reported to be effective in such transduction (38, 39). It is of note that AAV expressing inducible shRNAs targeting claudin-5, or a combination of claudin-5 and occludin have been used to transfect cerebral and retinal tissues, and that downregulation of these TJ vascular endothelial cell components renders the blood-brain and inner blood retina barriers reversibly permeable to compounds up to 1 kDa, or 5 kDa respectively (27, 28). Should it prove possible using this technique to periodically activate virus expressing short hairpin RNAs (shRNA) within SCEC using an inducible promoter, expression of such shRNA could in principle be used as a means of controlling IOP in cases of POAG in which patients fail to achieve target IOP with conventional medications. Alternatively, periodic episcleral delivery of siRNA, where materials can be delivered non-invasively into the outflow tissues in a retrograde fashion as an outpatient procedure (40), might represent an attractive alternative, thus avoiding the necessity of introducing a viral vector into the anterior chamber to secure periodic virally-mediated shRNA expression. To explore the feasibility of an episcleral delivery approach, we injected biotin conjugated tracer molecules via the episcleral route into mice, and were able to detect high levels of biotin in aqueous humour taken from the anterior chamber (FIG. 12a), as well as strong biotin staining in the conventional outflow pathway (FIG. 12b). Taken together, results from this study attest to the fact that endothelial tight junctions of the inner wall of Schlemm's canal are an attractive target for the treatment of primary and secondary forms of glaucoma.

The invention claimed is:

1. A method for the treatment of glaucoma in a subject comprising the step of administering an effective amount of an RNAi inducing agent capable of reducing the expression of one or more tight junction proteins expressed in the tight junction complex joining Schlemm's canal endothelial cells (SCEC) in an eye of the subject, wherein the RNAi inducing agent is selected from the group consisting of an RNAi agent, a nucleic acid vector encoding an RNAi agent, and a virus carrying a nucleic acid vector encoding an RNAi agent; and wherein the RNAi inducing agent is capable of reducing the expression of one or more tight junction proteins selected from the group consisting of claudin-11, Tricellulin and ZO-1.

2. The method of claim 1, wherein the RNAi inducing agent is selected from the group consisting of siRNA, shRNA and an RNAi-inducing vector whose presence within a cell results in production of an siRNA or shRNA.

3. The method of claim 1, wherein the glaucoma is a primary or secondary glaucoma.

4. The method of claim 1, wherein the RNAi inducing agent is administered locally to the eye.

5. The method of claim 1, wherein the RNAi inducing agent is administered by intracameral injection or inoculation.

6. The method of claim 1, wherein the RNAi inducing agent is administered episclerally into the aqueous humour outflow tissues.

7. The method of claim 1 wherein the subject is resistant or non-responsive to conventional pressure lowering medications.

8. The method according to claim 1, wherein said administration of said RNAi inducing agent reduces intra-ocular pressure in said eye of said subject.

9. The method of claim 3, wherein the primary glaucoma is primary open-angle glaucoma (POAG).

10. The method of claim 1, wherein the RNAi inducing agent is administered by viral mediated delivery.

11. The method according to claim 1, wherein said administration of said RNAi inducing agent reduces ocular hypertension in said eye of said subject.

12. The method according to claim 1, wherein said administration of said RNAi inducing agent results in the reversible and transient RNAi-mediated suppression of the tight junction complex joining Schlemm's canal endothelial cells.

* * * * *

SEQUENCE LISTING

```
<160> NUMBER OF SEQ ID NOS: 15

<210> SEQ ID NO 1
<211> LENGTH: 19
<212> TYPE: DNA
<213> ORGANISM: Artificial sequence
<220> FEATURE:
<223> OTHER INFORMATION: human claudin-11 siRNA

<400> SEQUENCE: 1
gtcatttact tgtacgaga                                              19
```

```
<210> SEQ ID NO 2
<211> LENGTH: 21
<212> TYPE: DNA
<213> ORGANISM: Artificial sequence
<220> FEATURE:
<223> OTHER INFORMATION: human claudin-11 siRNA sense strand with
      overhangs

<400> SEQUENCE: 2
gtcatttact tgtacgagat t                                         21

<210> SEQ ID NO 3
<211> LENGTH: 21
<212> TYPE: DNA
<213> ORGANISM: Artificial sequence
<220> FEATURE:
<223> OTHER INFORMATION: Human claudin-11 siRNA antisense strand with
      overhangs

<400> SEQUENCE: 3
tctcgtacaa gtaaatgacc t                                         21

<210> SEQ ID NO 4
<211> LENGTH: 19
<212> TYPE: DNA
<213> ORGANISM: Artificial sequence
<220> FEATURE:
<223> OTHER INFORMATION: human ZO-1 siRNA

<400> SEQUENCE: 4
cgatctcata aacttcgta                                            19

<210> SEQ ID NO 5
<211> LENGTH: 21
<212> TYPE: DNA
<213> ORGANISM: Artificial sequence
<220> FEATURE:
<223> OTHER INFORMATION: human ZO-1 siRNA sense strand with overhangs

<400> SEQUENCE: 5
cgatctcata aacttcgtat t                                         21

<210> SEQ ID NO 6
<211> LENGTH: 21
<212> TYPE: DNA
<213> ORGANISM: Artificial sequence
<220> FEATURE:
<223> OTHER INFORMATION: Human ZO-1 siRNA antisense strand with
      overhangs

<400> SEQUENCE: 6
tacgaagttt atgagatcgc t                                         21

<210> SEQ ID NO 7
<211> LENGTH: 19
<212> TYPE: DNA
<213> ORGANISM: Artificial sequence
<220> FEATURE:
<223> OTHER INFORMATION: Human MARVELD2 siRNA

<400> SEQUENCE: 7
ggattagctt ggatcacca                                            19

<210> SEQ ID NO 8
<211> LENGTH: 21
```

```
-continued

<212> TYPE: DNA
<213> ORGANISM: Artificial sequence
<220> FEATURE:
<223> OTHER INFORMATION: human MARVELD2  siRNA sense strand with
      overhangs

<400> SEQUENCE: 8
ggattagctt ggatcaccat t                                             21

<210> SEQ ID NO 9
<211> LENGTH: 21
<212> TYPE: DNA
<213> ORGANISM: Artificial sequence
<220> FEATURE:
<223> OTHER INFORMATION: human MARVELD2  siRNA antisense strand with
      overhangs

<400> SEQUENCE: 9
tggtgatcca agctaatcca g                                             21

<210> SEQ ID NO 10
<211> LENGTH: 19
<212> TYPE: DNA
<213> ORGANISM: Artificial sequence
<220> FEATURE:
<223> OTHER INFORMATION: Mouse ZO-1 siRNA

<400> SEQUENCE: 10
cattcgcctt catacaata                                                19

<210> SEQ ID NO 11
<211> LENGTH: 21
<212> TYPE: DNA
<213> ORGANISM: Artificial sequence
<220> FEATURE:
<223> OTHER INFORMATION: Mouse ZO-1 siRNA sense strand with overhangs

<400> SEQUENCE: 11
cattcgcctt catacaatat t                                             21

<210> SEQ ID NO 12
<211> LENGTH: 21
<212> TYPE: DNA
<213> ORGANISM: Artificial sequence
<220> FEATURE:
<223> OTHER INFORMATION: Mouse ZO-1 siRNA antisense strand with
      overhangs

<400> SEQUENCE: 12
tattgtatga aggcgaatga t                                             21

<210> SEQ ID NO 13
<211> LENGTH: 19
<212> TYPE: DNA
<213> ORGANISM: Artificial sequence
<220> FEATURE:
<223> OTHER INFORMATION: Mouse MARVELD2 siRNA

<400> SEQUENCE: 13
acgagagaat ttcaagaat                                                19

<210> SEQ ID NO 14
<211> LENGTH: 21
<212> TYPE: DNA
<213> ORGANISM: Artificial sequence
```

```
<220> FEATURE:
<223> OTHER INFORMATION: Mouse MARVELD2 siRNA sense strand with
      overhangs

<400> SEQUENCE: 14
acgagagaat tcaagaatt t                                            21

<210> SEQ ID NO 15
<211> LENGTH: 21
<212> TYPE: DNA
<213> ORGANISM: Artificial sequence
<220> FEATURE:
<223> OTHER INFORMATION: Mouse MARVELD2 siRNA antisense strand with
      overhangs

<400> SEQUENCE: 15
attcttgaaa ttctctcgtt t                                           21
```